(12) United States Patent
Phee et al.

(10) Patent No.: US 9,375,554 B2
(45) Date of Patent: Jun. 28, 2016

(54) BALLOON INFLATING DEVICE AND A METHOD FOR INFLATING A BALLOON

(75) Inventors: Soo Jay Louis Phee, Singapore (SG); Kai Juan Wong, Singapore (SG); Su Lim Tan, Singapore (SG); Andy Prima Kencana, Singapore (SG); Khek Yu Ho, Singapore (SG)

(73) Assignees: NATIONAL UNIVERSITY OF SINGAPORE, Singapore (SG); NANYANG TECHNOLOGICAL UNIVERSITY, Singapore (SG)

(*) Notice: Subject to any disclaimer, the term of this patent is extended or adjusted under 35 U.S.C. 154(b) by 588 days.

(21) Appl. No.: 13/695,278

(22) PCT Filed: May 3, 2011

(86) PCT No.: PCT/SG2011/000169
§ 371 (c)(1),
(2), (4) Date: Feb. 15, 2013

(87) PCT Pub. No.: WO2011/136745
PCT Pub. Date: Nov. 3, 2011

(65) Prior Publication Data
US 2013/0138132 A1    May 30, 2013

Related U.S. Application Data

(60) Provisional application No. 61/329,997, filed on Apr. 30, 2010.

(51) Int. Cl.
*A61M 29/00* (2006.01)
*A61M 29/02* (2006.01)
(Continued)

(52) U.S. Cl.
CPC .............. *A61M 29/02* (2013.01); *A61F 5/003* (2013.01); *A61F 5/0046* (2013.01); *A61M 25/1018* (2013.01); *A61M 2025/1054* (2013.01)

(58) Field of Classification Search
CPC ..... A61F 5/0003; A61F 5/003; A61F 5/0036; A61F 5/004; A61F 5/0046; A61F 5/0073; A61F 5/0033; A61F 5/0043; A61M 25/1018
See application file for complete search history.

(56) References Cited

U.S. PATENT DOCUMENTS

| 3,845,970 A | 11/1974 | Herrmann | |
|---|---|---|---|
| 2007/0156248 A1* | 7/2007 | Marco | A61F 2/02 623/23.7 |

(Continued)

FOREIGN PATENT DOCUMENTS

| EP | 0103481 A1 | 3/1984 |
|---|---|---|
| GB | 2448300 | 10/2008 |

(Continued)

OTHER PUBLICATIONS

International Search Report Dated Jun. 29, 2011 for International PCT Patent Application No. PCT/SG2011/000169 Filed on May 3, 2011.

(Continued)

*Primary Examiner* — Jonathan W Miles
*Assistant Examiner* — Kankindi Rwego
(74) *Attorney, Agent, or Firm* — Innovation Capital Law Group, LLP; Vic Lin

(57) ABSTRACT

According to various embodiments, a balloon inflating device may be provided. The balloon inflating device may include a balloon, a first substance within the balloon, a second substance within the balloon capable of having a reaction with the first substance to generate a gas within the balloon to inflate the balloon; and an electrical activator configured to activate the reaction between the first and second substances thus inflating the balloon. According to various embodiments, a method for inflating a balloon may be provided. The method for inflating a balloon may include providing a first substance within the balloon, providing a second substance within the balloon; and activating a reaction between the first and second substances electrically to generate a gas within the balloon to inflate the balloon.

15 Claims, 23 Drawing Sheets

(51) Int. Cl.
*A61F 5/00* (2006.01)
*A61M 25/10* (2013.01)

(56) References Cited

U.S. PATENT DOCUMENTS

2008/0269664 A1* 10/2008 Trovato .............. A61B 1/00016
604/20
2010/0100117 A1* 4/2010 Brister .................... A61F 5/003
606/192

FOREIGN PATENT DOCUMENTS

| WO | 87/00034 | 1/1987 |
|---|---|---|
| WO | 2006/075944 A1 | 7/2006 |
| WO | 2010/045482 A2 | 4/2010 |

OTHER PUBLICATIONS

Notification of Transmittal of International Preliminary Report on Patentability (mailing date Aug. 23, 2012) for International PCT Patent Application No. PCT/SG2011/000169 Filed on May 3, 2011.
Written Opinion of the International Searching Authority (mailing date Jun. 29, 2011) for International PCT Patent Application No. PCT/SG2011/000169 Filed on May 3, 2011.

* cited by examiner

BALLOON INFLATING DEVICE AND A METHOD FOR INFLATING A BALLOON

CROSS-REFERENCE TO RELATED APPLICATIONS

This application claims the benefit of PCT/US2011/000169, filed May 3, 2011 which claims the benefit of priority of U.S. provisional application No. 61/329,997, filed Apr. 30, 2010, the contents of these being hereby incorporated by reference in their entirety for all purposes.

TECHNICAL FIELD

Various embodiments generally relates to a balloon inflating device and a method for inflating a balloon.

BACKGROUND

There are many devices available in the market to aid a person in losing weight. Intragastric balloon has become one of the popular treatments for losing weight because it is considered a non-surgical procedure and non-pharmaceutical treatment. When in use, the balloon is placed in the stomach and inflated so that it will partially fill the stomach to give the feeling of satiety. The balloon would stay in the stomach for a period of time and over time, the person may lose weight. At the end of the treatment, it would be removed surgically. There have been several disclosures of intragastric balloon previously.

In U.S. Pat. No. 4,133,315 (Berman et al.), it disclosed a system which includes an inflatable bag and a flexible tube attached to it. The bag is to be swallowed by the user and the tube extends from the bag, through the user's esophagus and out from his or her nasal cavity or mouth. To inflate the bag, fluid is supplied from the free end of the tube. Once inflated, the bag will occupy some volume in the user's stomach, and hence reduce the amount of food intake by the user to feel satiety. Alternatively, the tube extends from the bag through the stomach wall. However this system is not desirable because it is uncomfortable to have a tube in the esophagus, or it involves surgery to insert the balloon. Further, this system requires an endoscopic procedure to insert the balloon which may cause the user discomfort.

In U.S. Pat. No. 6,579,301, it disclosed a bladder inflating device which consists of a flexible bladder, a relatively rigid reservoir attach to the bladder, and an inflation/deflation system that permits the movement of the fluid from the reservoir into the bladder. Various systems were disclosed to move or permit movement of the fluid e.g. a pump system using the piston and spring force to pump the fluid from the reservoir into the bladder, a heating element to boil the fluid and make the fluid expand through a valve to inflate the bladder, and a thermally conductive bladder to boil the fluid inside the bladder by a hot liquid consumed by the user. The system is battery powered and has a control system to automatically activate the inflation/deflation system or is activated by surrounding conditions e.g. temperature or pressure in the stomach. The disclosure is not desirable due to several reasons. Firstly, the usage of a pump would require large power consumption and power consumption is an aspect in intragastric balloon system. Secondly, the heating element may require even larger power consumption and the temperature imbalance may irritate or injure the user.

SUMMARY

According to various embodiments, a balloon inflating device may be provided.

The balloon inflating device may include a balloon, a first substance within the balloon, a second substance within the balloon capable of having a reaction with the first substance to generate a gas within the balloon to inflate the balloon; and an electrical activator configured to activate the reaction between the first and second substances thus inflating the balloon.

According to various embodiments, a method for inflating a balloon may be provided.

The method for inflating a balloon may include providing a first substance within the balloon, providing a second substance within the balloon; and activating a reaction between the first and second substances electrically to generate a gas within the balloon to inflate the balloon.

BRIEF DESCRIPTION OF THE DRAWINGS

The invention will be better understood with reference to the detailed description when considered in conjunction with the non-limiting examples and the accompanying drawings, in which.

DETAILED DESCRIPTION

The features described in an embodiment are not restricted to that embodiment and may be used in other embodiments. Also, the method described herein may be translated to a device and vice versa.

The embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the embodiments have been specifically disclosed and optional features, modification and variation of the inventions embodied therein herein disclosed may be resorted to by those skilled in the art, and that such modifications and variations are considered to be within the scope of this invention.

Figure 1A:
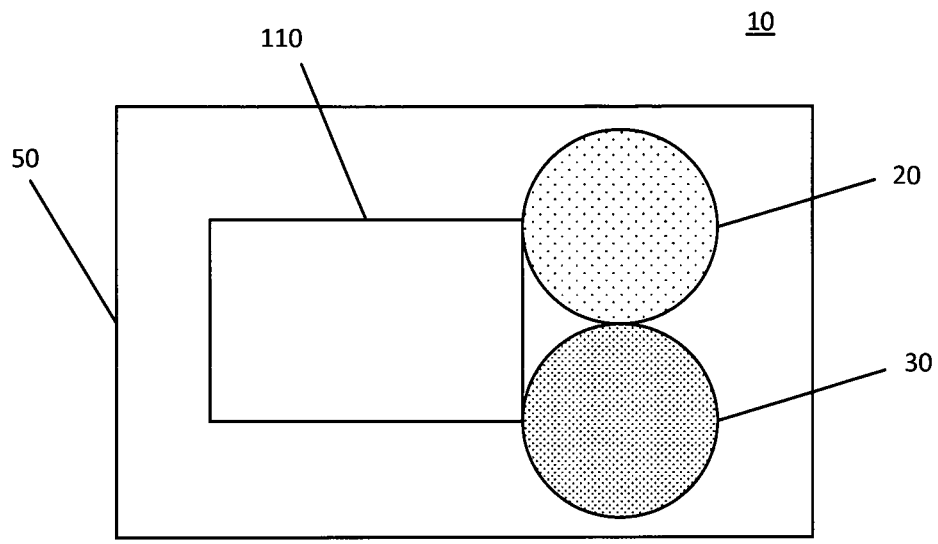
FIG. 1A shows a schematic diagram of an embodiment of a balloon inflating device.

FIG. 1A shows a schematic diagram of a balloon inflating device 10 having a balloon 50, a first substance 20 and a second substance 30 within the balloon 50 and an electrical activator 110 configured to activate a reaction between the first substance 20 and the second substance 30.

Figure 1B:
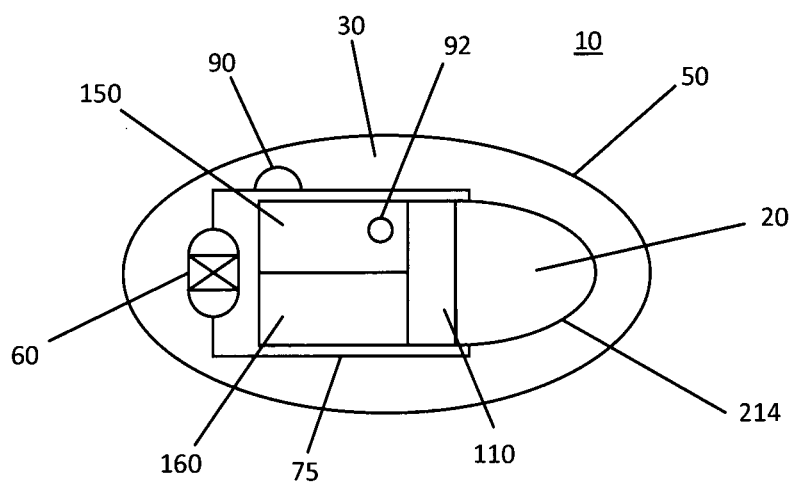
FIG. 1B shows a schematic diagram of an embodiment of a balloon inflating device.

FIG. 1B shows a schematic diagram of an embodiment of device 10. As in FIG. 1, the first substance 20 and second substance 30 are within the balloon 50. The electrical activator 110 is within the balloon 50. Further, there is a controller 150 configured to control the electrical activator 110. There may also be a receiver 160 connected to the controller 150 and configured to receive a remote signal and sending the signal to the controller 150. There may be a separator 214 configured to separate the first substance 20 from the second substance 30 and the separator 214 can be activated by the electrical activator 110 to allow contact between the first substance 20 and second substance 30. There may be a casing 75 for containing the controller 150 and the receiver 160. There may be a valve 60 configured to release a gas (not shown) from the balloon 50. There may be one or more sensors 90 for measuring one of more of the following properties: temperature, humidity, acidity, pressure and position. There may be a timer 92 configured to activate the reaction between the first substance 20 and second substance 30 at a predetermined time.

The electrical activator 110 may include a syringe (not shown) having a plunger (not shown) and an actuator (not shown) configured to drive the plunger wherein the syringe contains the first substance 20 and the actuator is configured to, when activated electrically, drive the plunger and actuates the first substance 20 to contact the second substance 30.

The actuator may include a stopper (not shown) and a resilient member (not shown) held compressed by the stopper wherein the stopper is configured to, when activated electrically, release the resilient member to drive the plunger.

The electrical activator 110 may include a biasing member (not shown) torsioned and attached to the separator 114 and a heating point (not shown) configured to heat the biasing member wherein the heating point is configured to, when activated electrically, heat the biasing member and release the biasing member thus releasing the separator 214 to allow contact between the first and second substances 20, 30.

The device 10 may include a press-fit cover (not shown) wherein releasing the biasing member releases the press-fit cover and separator 214.

The electrical activator 110 may include electrodes (not shown), wherein the separator 214 is in electrical contact with and between the electrodes, wherein the electrodes are configured to, when activated electrically, allow the first substance 20 to permeate the separator 214 to contact the second substance 30.

The electrical activator 110 may include a heating element (not shown) wherein the heating element is configured to, when activated electrically, melt the separator 214 to allow the first substance 20 to contact the second substance 30.

The separator 214 may include a membrane (not shown).

The electrical activator 110 may include an energy source (not shown) wherein the energy source, when activated electrically, energizes the first and second substances 20, 30 to react with each other.

The device 10 may include a dissolvable substance (not shown) configured to retain the balloon 50 in a compressed configuration.

The dissolvable substance may be a coating (not shown) wherein the coating is coated onto the balloon 50.

The device 10 may include a heater (not shown) in communication with the controller 150 configured to heat the balloon 50 wherein the heater is capable of heating the balloon 50 and puncturing it to release the gas from the balloon 50.

The balloon 50 may include a material (not shown) which degenerates over a predetermined time period when exposed to an acid (not shown).

The balloon 50 may include a heat source (not shown), a shape memory alloy (not shown) in thermal contact with the heat source configured to distort with the balloon 50 from an original shape when the balloon 50 is inflated wherein the balloon 50 is returned to the original shape when the shape memory alloy is heated.

The first substance 20 may be a bicarbonate and the second substance 30 may be an acid capable of reacting with the bicarbonate to generate the gas.

The balloon may include a multi-layered membrane (not shown).

The multi-layered membrane may include a layer of plastic film (not shown) and a layer of rubber (not shown).

The layer of plastic may have a thickness lesser than 30 microns.

The balloon may include a radio-opaque substance.

The device 10 may include a channel (not shown) configured to release the gas wherein the plunger, the channel comprising an opening wherein the plunger when retracted exposes the opening to allow the gas to be released through the channel.

The casing may be made of an organic thermoplastic and the organic thermoplastic may include Polyether Ether Ketone (PEEK).

Figure 1C:
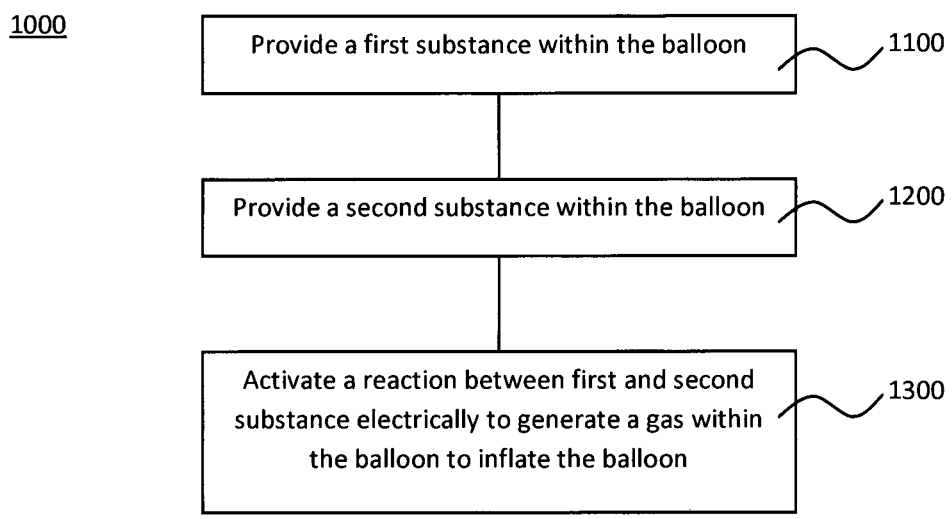
FIG. 1C shows a flow diagram illustrating a method for inflating a balloon.

FIG. 1C shows a flow diagram 1000 illustrating a method for inflating a balloon 50. In 1000, a first substance is provided within the balloon 50. In 1200, a second substance is provided within the balloon 50 and in 1300 a reaction between the first substance and second substance is activated electrically to generate the gas within the balloon 50 to inflate the balloon 50.

The method may include controlling the activating of the reaction between the first and second substances 20, 30.

The method may include receiving a remote signal and sending the signal to control the reaction.

The method may include driving a plunger in a syringe containing the first substance 20 and actuating the first substance 20 to contact the second substance 30.

The method may include electrically activating a stopper to release a compressed resilient member and releasing the resilient member to drive the plunger.

The method may include activating the reaction electrically includes activating a separator 114 to allow the contact between the first and second substances 20, 30.

The method may include heating a torsioned biasing member attached to the separator 114, releasing the biasing member and releasing the separator 114 to allow contact between the first and second substances 20, 30.

The method may include heating a torsioned biasing member attached to a press-fit cover, releasing the biasing member and releasing the press-fit cover and separator to allow contact between the first and second substances 20, 30.

The method may include activating the reaction electrically includes activating a separator electrically and allowing the first substance to permeate the separator to contact the second substance.

The method may include heating a heating element and melting the separator to allow the first substance 20 to contact the second substance 30.

The method may include energizing the first and second substances 20, 30 to react with each other.

The method may include dissolving a dissolvable substance to release the balloon 50.

The method may include dissolving a coating coated onto the balloon 50.

The method may include releasing the gas from the balloon 50 through a valve.

The method may include heating a heater and puncturing the balloon 50 to release the gas.

The method may include exposing the balloon 50 to an acid and degenerating the balloon 50 over a predetermined time.

The method may include heating a shape memory alloy to return to an original shape.

The method may include one or more of the following: sensing temperature, sensing humidity, sensing acidity, sensing pressure and sensing position.

The method may include providing a bicarbonate and providing an acid capable of reacting with the bicarbonate to generate the gas.

The method may include retracting the plunger to expose a channel and channeling the gas.

The method may include determining a time period and activating the reaction after the time period.

Figure 2A:
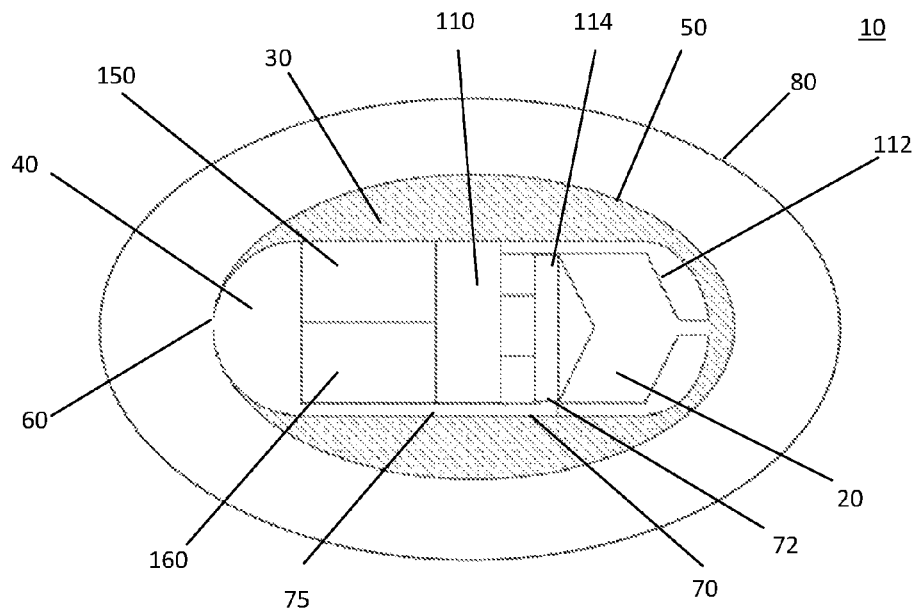
FIG. 2A shows a cross-sectional view of an embodiment of a balloon inflating device.

FIG. 2A shows the balloon inflating device 10 having an electrical activator 110, a controller 150, a receiver 160, the first substance 20, the second substance 30, a power supply 40, the balloon 50, a deflation outlet 60, a channel 70, a casing 75 and a dissolvable substance 80.

The controller 150, which may also be referred to as a main controller, is placed within the casing 75 and controls the electrical activator 110 to activate the reaction between the first substance 20 and second substance 30. The controller 150 includes a low-power microcontroller (MCU) and sensor interfaces (e.g. for temperature, humidity, pH, etc). The controller 150 is used to provide the necessary drivers and controllers for the device 10 as well as voltage regulation for various other components as well as a wireless RF transceiver.

The receiver 160, which may also be referred to as a communication hub, may include a RF transceiver and position tracking system that enable the remote control and monitoring of the device. The receiver 160 is connected to the controller 150 and is capable of receiving a remote signal and sending the signal to the controller 150.

According to various embodiments, the electrical activator 110 may include a syringe 112 which has a plunger 114 therein. In the syringe 112 is the first substance 20. The first substance 20 is separated from the second substance 30. The second substance 30 surrounds the casing 75 and within the balloon 50, before activation. The plunger 114 is actuated by an actuator (not shown). The actuator can be any linear motion system (not shown) e.g. motorized rack and pinion system and the linear motion system draws power from the power supply 40.

The power supply 40 includes a battery which is conventionally used for medical implant or device purposes.

The casing 75 is used to house the controller 150, the receiver 160, the power supply 40 and the electrical activator 110 which stores the first substance 20. At one end of the casing 75 is a deflation outlet 60 for release of gas which will be described later. The casing 75 may be made from materials used for implantable medical devices i.e. biocompatible and may be a non-digestible plastic enclosure. The casing 75 allows complete isolation of the components from the external environment e.g. user's stomach. The casing 75 may be made from an organic thermoplastic, Polyether Ether Ketone (PEEK). However, other materials like Pellethane 2363 Polytherurethane, PurSi and CarboSil may be used. The casing 75 may be of a capsule profile as shown in FIG. 1 and can either be attached the balloon 50 or lie within it. Therefore, the attachment parameters may be considered when choosing the material for the casing 75.

Between the syringe 112 and the deflation outlet 60 is a channel 70 for channeling the gas 22 from the balloon 50 to the outside of casing 75. The channel 70 has an opening 72 which is located at the rear part of the syringe 112 and covered by the plunger 114 before inflating the balloon 50.

The balloon 50 wraps around the casing 75 as shown in FIG. 1 and has a multi-layered configuration. The balloon 50 may be made of a gas barrier material and be non-toxic to the human body. Further, the balloon 50 has to be able to withstand strong hydrochloric acid in the stomach region. Moreover, the balloon 50 may be elastic, so that it is able to shrink back considerably after deflation to enable the casing 75 (together with the balloon 50) to leave the user's body through the normal digestion process. To achieve a high gas barrier quality and good elasticity, a thin layer of plastic film can be used as the inner lining of the balloon 50 to prevent gas from leaking and a layer of rubber material can be used as the outer layer of the balloon 50 to provide elasticity to shrink the balloon 50 back during deflation (to be shown later). With respect to the size of the casing 75, the thickness of the inner layer may be less than 30 micrometers so that the whole thickness of the balloon 50 may be less than 50 micrometers. The balloon 50 may be elastic as shown or non-elastic. The balloon 50 may include a single layer membrane. In addition, the balloon 50 may contain radio-opaque substance to allow visualization of the profile of the balloon 50 when it is in the user's body by X-ray. The balloon 50 may also be made from liquid impermeable and biocompatible membrane such as natural rubber, latex, polyethylene, nylon, silicone, and the like.

In the embodiment as shown in FIG. 2A, the first substance 20 may be an acid solution reactable with a bicarbonate solution and the second substance 30 may be Sodium Bicarbonate solution ($NaHCO_3$). The acid solution when contacted with the Sodium Bicarbonate solution reacts with the solution to generate carbon dioxide gas ($CO_2$). This reaction is commonly found in food industry. Alternatively, the acid solution may be Acetic Acid ($CH_3COOH$) or Citric Acid ($C_6H_8O_7$).

Figure 2B:
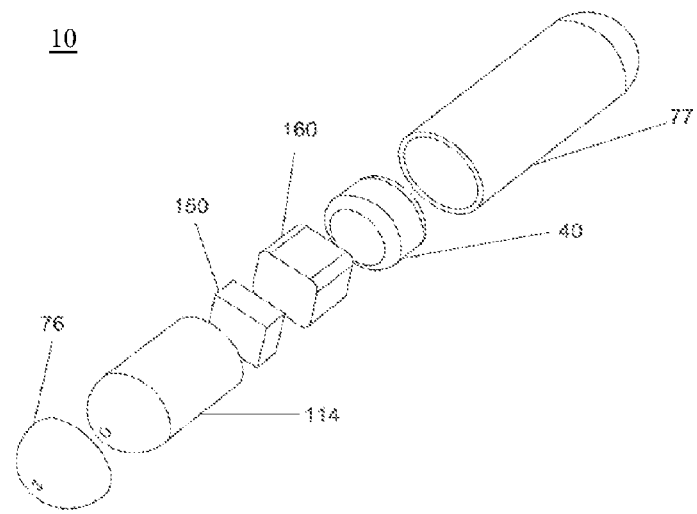
FIG. 2B shows a perspective view of an embodiment of a balloon inflating device.

FIG. 2B shows a perspective view of an embodiment of a balloon inflating device 10. The device 10 includes the casing 75 which includes end cap 76 and capsule enclosure 77, controller 150, receiver 160 and power supply 40.

Figure 3:
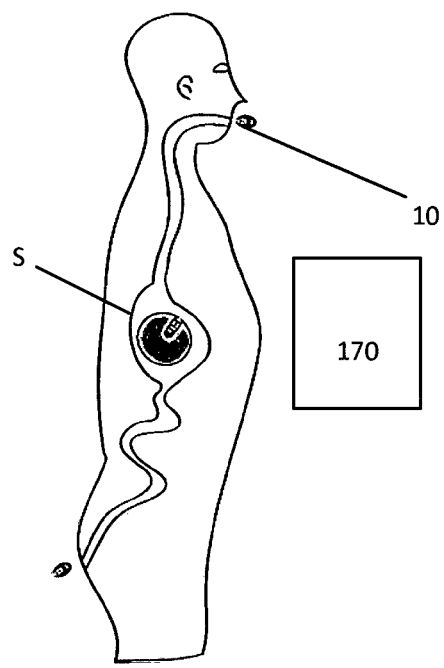
FIG. 3 shows a cross-sectional view of the embodiment of FIG. 2 when in use.

FIG. 3 shows the embodiment of FIG. 2A when in use. In FIG. 3, the device 10 is swallowed by the user, may be with a glass of water and it goes down the esophagus and into the user's stomach S. Once in the stomach S, the dissolvable substance 80 dissolves when it contacts the stomach acid in stomach S. The dissolving of the dissolvable substance 80 allows the balloon 50 space to inflate.

Figure 4:
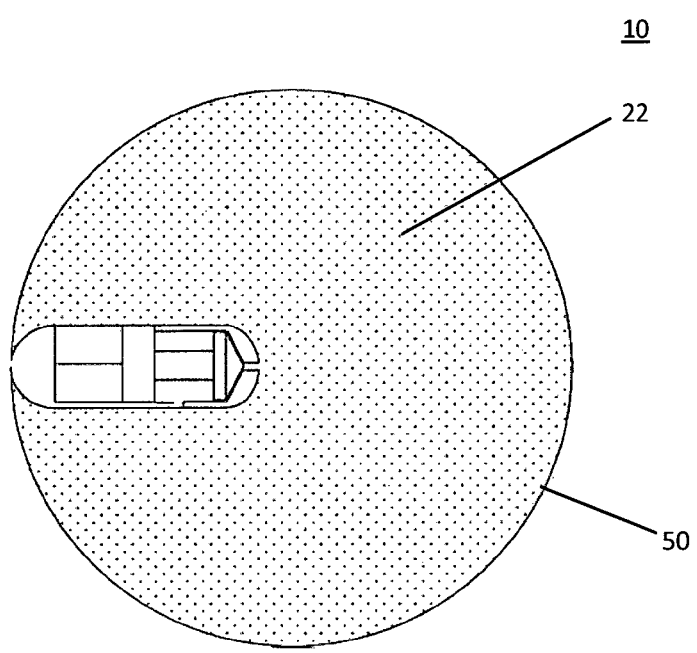
FIG. 4 shows a cross-sectional view of the embodiment of FIG. 2 after the balloon has been inflated.

FIG. 4 shows the embodiment of FIG. 2A after the balloon 50 has been inflated. To inflate the balloon 50, the receiver 160 receives a control signal from an external control system 170 and the receiver 160 sends the control signal to the controller 150. Upon receiving the control signal, the controller 150 activates the actuator to drive the plunger 114 along the syringe 112. As mentioned earlier, the actuator can be a linear motion system and drives the plunger 114 to slide along the syringe 112. The plunger 114 exerts sufficient radial friction on the inner cylinder wall of the syringe 112 to prevent any gas leakage via the plunger-cylindrical wall interface.

Due to the force exerted by the actuator onto the plunger 114, the first substance 20 in the syringe 112 is pushed out of the syringe 112. Once the first substance 20 leaves the syringe 112, it contacts the second substance 30 and reacts instantaneously. This reaction generates a gas 22 ($CO_2$) as shown in FIG. 4, and inflates the balloon 50. As more of first substance 20 reacts with the second substance 30, the amount of gas 22 increases and the balloon 50 inflates further. FIG. 4 shows the inflated balloon 50 when the balloon 50 is at its largest volume.

Once the balloon 50 reaches the desired volume, the device 10 will be kept in the user's stomach for a duration that is determined by a physician.

If the largest volume of the balloon 50 of one device 10 is still smaller than the desired volume for the treatment, the user may be encouraged to swallow another device 10 such that the total volume of the balloons 50 of the devices 10 can meet the desired volume for treatment. The device 10 may also be taken simultaneously with another device 10. The number of devices used simultaneously, period of usage and volume of the balloon 50 may be varied depending on clinical studies to optimize the device effectiveness.

Figure 5:
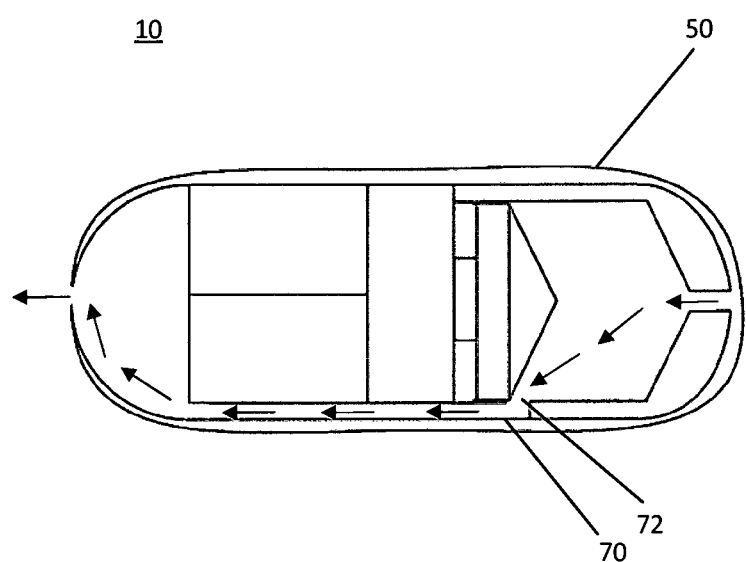
FIG. 5 shows a cross-sectional view of the embodiment of FIG. 4 with retracted plunger.

FIG. 5 shows the embodiment of FIG. 4 when the plunger 114 is retracted to let the gas 22 out. Once the desired duration is reached, the balloon 50 is deflated to allow the device 10 to be expelled from the user's stomach S. To deflate the balloon 50, another control signal is transmitted from the external control system 170 and received by the receiver 160. Upon receipt, the receiver 160 sends the signal to the controller 150 and the controller 150 activates the actuator 116 to retract the plunger 114. The deflation process takes place when the plunger 114 is retracted sufficiently to expose the opening 72 to the channel 70. This allows the gas 22 to flow out of the casing 75 as depicted in FIG. 5. The balloon 50 is deflated by the pressure in the stomach S and when deflated sufficiently, the device 10 can be passed out from the user's body through the lower gastrointestinal tract naturally.

Although not shown in the figures, a pressure sensor may be equipped in the device 10 in order to provide information on the volume of the balloon 50 during inflation. The pressure may be calculated using a mathematical model to estimate the volume of the inflated balloon 50. An actuator control method may be used to control the position of the plunger 114 to determine the amount of first substance 20 to be pushed out of the syringe 112 so as to control the volume of the balloon 50. The maximum volume of the balloon 50 is achieved when the plunger 114 is moved to a maximum distance in the syringe 112 e.g. at the tip of syringe 112, or when the first substance has been completely discharged from the syringe 112.

The volume of the balloon 50 may be calculated from a mathematical model as shown below:

In the various embodiments, the balloon 50 may be made of natural rubber or latex. For the purpose of modeling the inflation and deflation of the balloon 50, a mathematical formula is used, namely the filling radius equation for rubber balloon:

$$\frac{N(r)}{N(r_0)} = \left[1 + \frac{2s_+ d_0}{p_0 r_0}\left(\frac{r_0}{r} - \left(\frac{r_0}{r}\right)^7\right)\left(1 - \frac{s_-}{s_+}\left(\frac{r}{r_0}\right)^2\right)\right]\left(\frac{r}{r_0}\right)^3 \quad (1)$$

Where:
$N(r)$=The amount of gas (in mol) required to inflate the balloon to radius r
$N(r_0)$=The amount of gas (in mol) of the initial volume
$s_+$, $s_-$=Temperature dependent elastic coefficient of the balloon
  r=Radius of the un-distorted balloon (mm)
  r=Balloon radius at pressure P (mm)
  $d_0$=Balloon thickness (mm)
  From this equation, having known the amount of gas $N(r)$ inserted to a rubber balloon, the radius of the inflated balloon 50 can be calculated and hence the volume of the balloon 50 can be obtained. For example, for the gas generated from the reaction of Acetic Acid and Sodium Bicarbonate, the chemical equation for the reaction is:

$$CH_3COOH(aq) + NaHCO_3(s) \rightarrow CH_3COONa(aq) + CO_2(g) + H_2O(l) \qquad (2)$$

From this equation, the amount of carbon dioxide ($CO_2$) gas generated can be obtained using basic chemistry stoichiometry and it is the N(r) of the filling radius equation above. Therefore by using these two equations, the volume of the inflated balloon 50 can be calculated by having the amount of moles of Acetic Acid and Sodium Bicarbonate as the input parameters.

Figure 6:
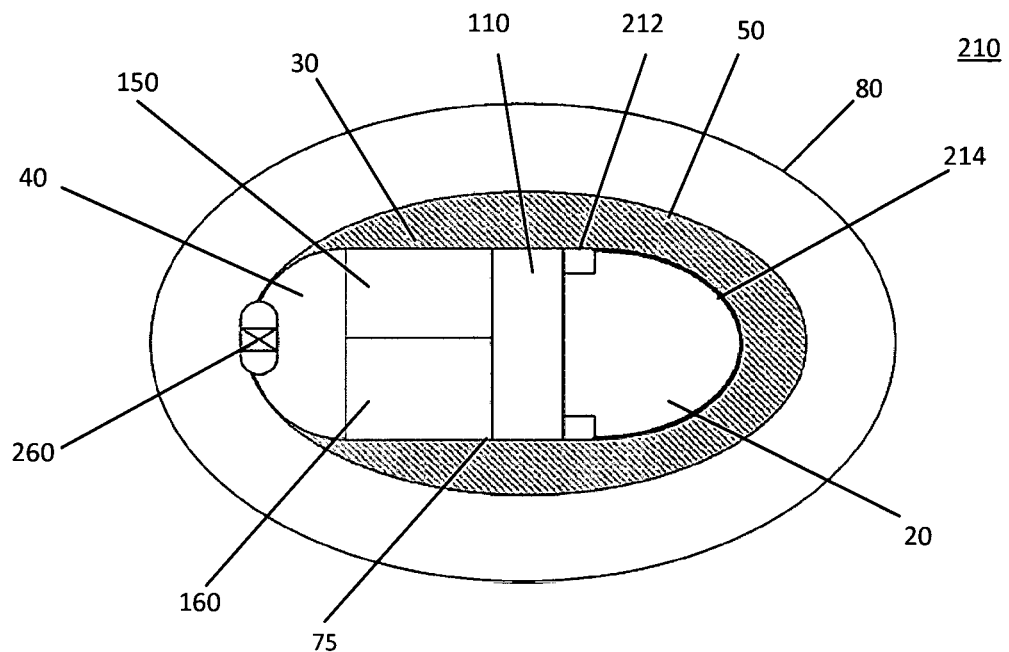
FIG. 6 shows a cross-sectional view of an embodiment wherein the electrical activator includes an electrode and a separator.

FIG. 6 shows an embodiment wherein the electrical activator 110 includes an electrode 212 and a separator 214 configuration. Various components shown are identical to components described above and the same reference signs may be used so that duplicate description may be omitted. The electrical activator 110 includes the electrodes 212 and the separator 214 is in electrical contact with and between the electrodes 212. The first substance 20 is stored between the casing 75 and the separator 214 and the second substance 30 is stored within the balloon 50 thereby prevented from mixing with the first substance 20 by the separator 214. In addition, at one end of the casing 75 is a normally closed valve 260 for controlling the release of the gas (not shown) during the deflation of the balloon 50.

The electrodes 212 are attached at the edge of the membrane and provide a voltage difference to the separator 214.

The separator 214 has two permeability configurations depending on the voltage across the electrodes 212. And altering the voltage across the electrodes 212 toggles the permeability of the separator 214 between permeable and impermeable configuration. The separator 214 may be a membrane.

The first substance 20 may be an acid solution and the second substance 30 may be Sodium Bicarbonate.

The dissolvable substance 80 dissolves when it contacts the stomach acid, hence allowing the balloon to inflate.

Figure 7:
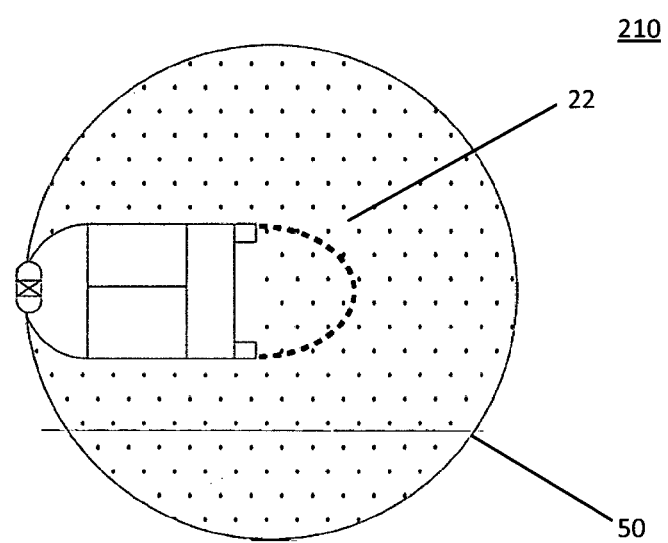
FIG. 7 shows a cross-sectional view of the embodiment in FIG. 6 after the balloon has been inflated.

FIG. 7 shows the embodiment of FIG. 6 after the balloon 50 has been inflated. Upon receiving a control signal, the receiver 160 sends the control signal to the controller 150 and the controller 150 activates the electrodes 212. The voltage of the electrodes 212 changes and thus changes the permeability of the separator 214 such that the first substance 20 is able to flow through the separator 214 and contacts the second substance 30 and reacts with the second substance 30. From the reaction, the gas 22 is generated and inflates the balloon 50 as depicted in FIG. 7.

Once the balloon 50 reaches the desired volume, the device 210 is kept in the user's stomach S for the duration that is determined by the physician. If the largest volume of one balloon is still smaller than the desired volume for the treatment, the user may be encouraged to swallow another device 210 such that the total volume of the balloons 50 of the devices 210 can meet the desired volume for treatment.

As the separator 214 changes its permeability, the mechanical property of the separator 214 is weakened to an extent that it is easy to break away from the electrode 212 when it is subjected to any pressure change. The valve 260 enables the pressure in the balloon 50 to be high so that the volume of the balloon 50 would increase. The maximum volume of the balloon 50 is achieved when the first substance 20 has fully reacted with the second substance 30. FIG. 7 shows the inflated balloon 50 when the balloon 50 is at its largest volume.

Figure 8A:
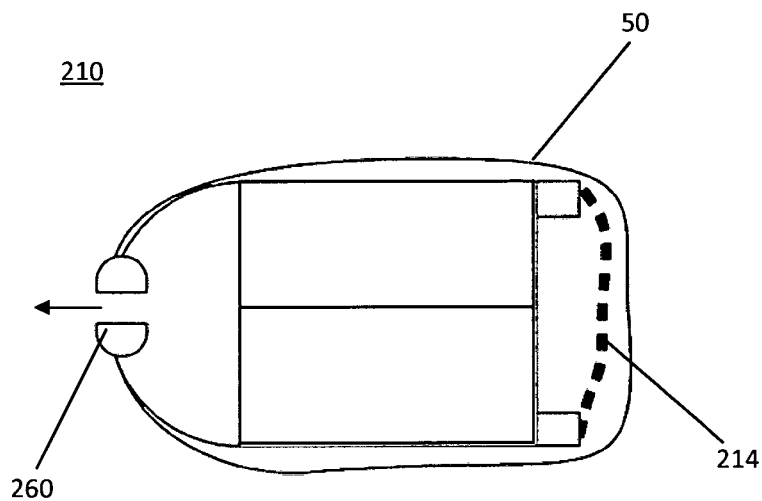
FIG. 8A shows a cross-sectional view of the embodiment in FIG. 7 when deflated.

FIG. 8A shows the embodiment of FIG. 7 with the valve 260 opened to let the gas 22 out. Once the desired duration is reached, the balloon 50 is deflated to allow the device 210 to be expelled from the user's stomach S. To deflate the balloon 50, another control signal is received by the receiver 160.

Figure 8B:
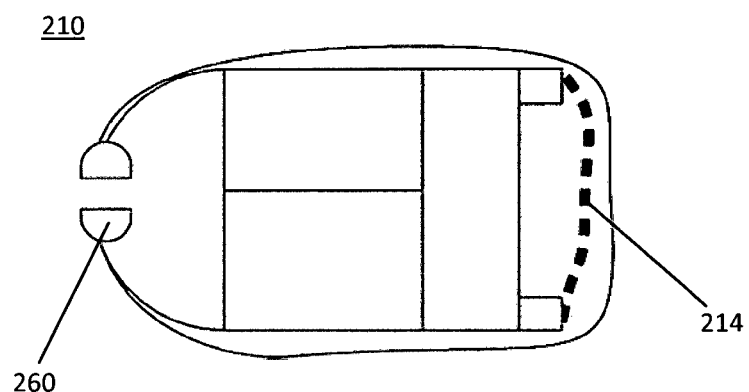
FIG. 8B shows the embodiment in FIG. 7 when deflated.

FIG. 8B shows the embodiment in FIG. 7 when deflated. Upon receipt, the receiver 160 sends the signal to the controller 150 and the controller 150 activates the valve 260 to open it so that the gas 22 can flow out of the casing due to the pressure difference between the stomach S and the balloon 50. This will allow the gas 22 to flow out of the casing 75 as depicted in FIG. 8. When deflated sufficiently, the device 210 can be passed out from the user's body through the lower gastrointestinal tract naturally.

Figure 9:
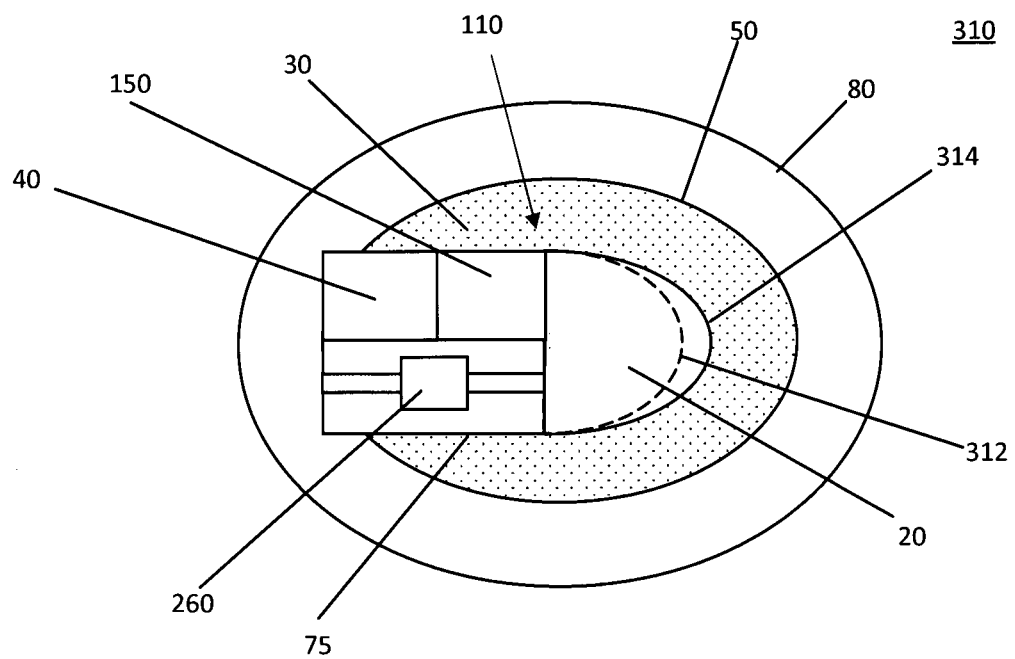
FIG. 9 shows a cross-sectional view of an embodiment wherein the electrical activator includes a separator and heating element configuration.

FIG. 9 shows an embodiment wherein the electrical activator 110 includes a separator 314 and heating element 312 configuration. Various components shown are identical to components described above and the same reference signs may be used so that duplicate description may be omitted. According to various embodiments, the electrical activator 110 includes a heating element 312 and a separator 314. The first substance 20 is stored between the casing 75 and the separator 314 and the second substance 30 is stored within the balloon 50 thereby prevented from mixing with the first substance 20 by the separator 314. The normally closed valve 260 is located in the casing 75 for controlling the release of the gas (not shown) during the deflation of the balloon 50.

The heating element 312 may be a soft and thin conductor filament that is reinforced under the separator 314. When activated, electric current is passed along the heating element 312 by applying voltage across the heating element 312. The electrical energy is converted to thermal energy in the heating element 312.

The separator 314 may be a low temperature barrier membrane. The separator 314 has a relatively low melting temperature which is slightly higher than the human body temperature, for example between 34 and 38° C.

The first substance 20 may be an acid solution and the second substance 30 may be Sodium Bicarbonate.

The dissolvable substance 80 dissolves when it contacts the stomach acid, hence allowing the balloon to inflate.

Figure 10A:
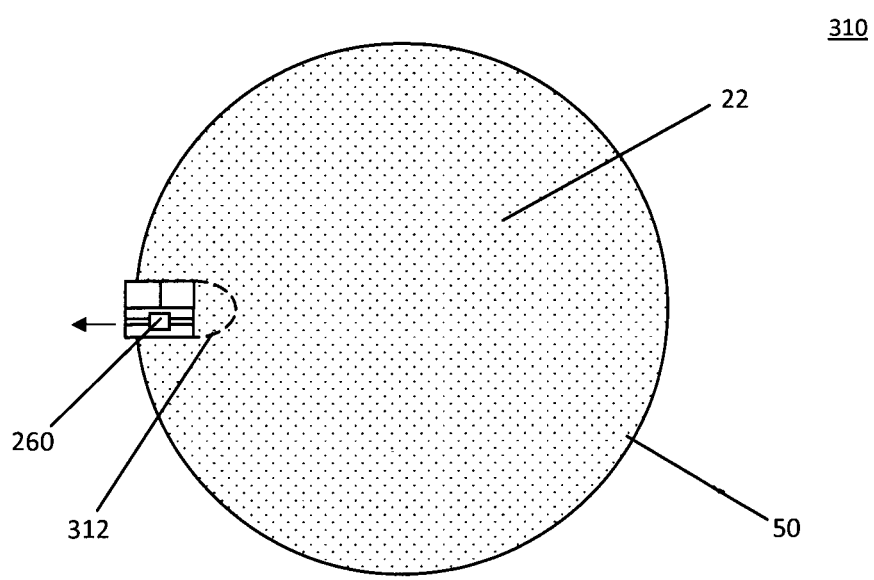
FIG. 10A shows a cross-sectional view of the embodiment in FIG. 9 after the balloon has been inflated.

FIG. 10A shows the embodiment in FIG. 9 after the balloon 50 has been inflated. Although it is not shown in FIG. 9, the receiver (not shown) may be incorporated in the design to allow remote control. Upon receiving a control signal, the receiver sends the control signal to the controller 150 and the controller 150 activates the heating element 312 by passing electric current along it. The heating element 312 dissipates heat and increases the surrounding temperature of the separator 314 adjacent the heating element 312. The separator 314 melts (when the surrounding temperature reaches the membrane melting temperature) and creates an opening in the separator 314. As the separator 314 is a low temperature barrier membrane, it may be subjected to its maximum tension under the heat and held in tension around the casing 75 until the separator 314 breaks down completely (propagation impulse effect). Once broken, the first substance 20 contacts the second substance 30 and reacts with the second substance 30. From the reaction, the gas 22 is generated and inflates the balloon 50 as depicted in FIG. 10. The maximum volume of the balloon 50 is achieved when first substance 20 has fully reacted with the second substance 30.

Once the desired duration of treatment is reached, the balloon 50 is deflated to allow the device 310 to be expelled from the user's stomach S. To deflate the balloon 50, another control signal is received by the receiver.

Figure 10B:
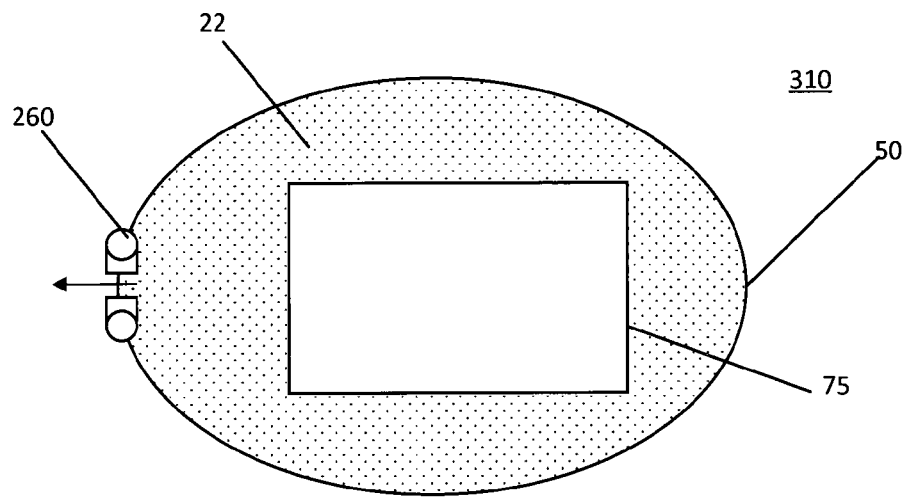
FIG. 10B shows an embodiment in FIG. 10B with an open valve for gas to escape.

FIG. 10B shows an embodiment in FIG. 10B with an open valve for gas to escape. Upon receipt, the receiver sends the signal to the controller 150 and the controller 150 activates the valve 260 to open it so that the gas 22 can flow out (see arrow) of the casing due to the pressure difference between the stomach S and the balloon 50. When deflated sufficiently, the device 310 can be passed out from the user's body through the lower gastrointestinal tract naturally.

Figure 11:
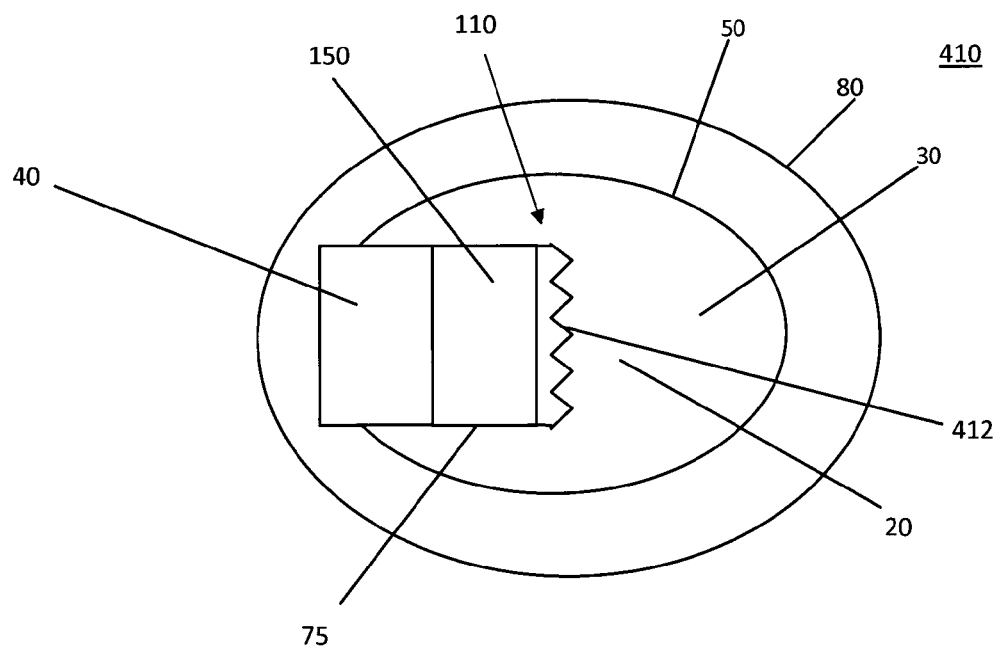
FIG. 11 shows a cross-sectional view of an embodiment wherein the electrical activator includes an energy source.

FIG. 11 shows an embodiment wherein the electrical activator 110 includes an energy source 412. The first substance 20 and the second substance 30 are stored within the balloon 50.

The first substance 20 and second substance 30 are chosen such that each substance requires a certain amount of energy to activate a reaction between them.

The dissolvable substance 80 dissolves when it contacts the stomach acid, hence allowing the balloon to inflate.

Although it is not shown in FIG. 11, the receiver (not shown) may be incorporated in the design to allow remote control. Upon receiving a control signal, the receiver sends the control signal to the controller 150 and the controller 150 activates the energy source 412. The energy source 412 generates energy required to energize the chemical reaction between the first substance 20 and the second substance 30. From the reaction, the gas 22 is generated and inflates the balloon 50 as in the previous embodiments. The maximum volume of the balloon 50 is achieved when first substance 20 has fully reacted with the second substance 30.

Once the desired duration of treatment is reached, the balloon 50 is deflated to allow the device 410 to be expelled from the user's stomach S. Although it is not shown in FIG. 11, the valve 260 (not shown) may be used to deflate the balloon 50. The balloon 50 may also be deflated by puncturing it by degeneration. The material of the balloon 50 may be chosen to degenerate when in contact with the strong hydrochloric acid in the stomach. When degenerated, the gas 22 is able to flow from the balloon 50 into the stomach.

This embodiment allows easy assembly of the device 410 as there are lesser sub-assemblies to be fitted in the casing 75. However, the embodiment may require a longer period of time to allow the energy activation (to change between states) to happen.

Figure 12:
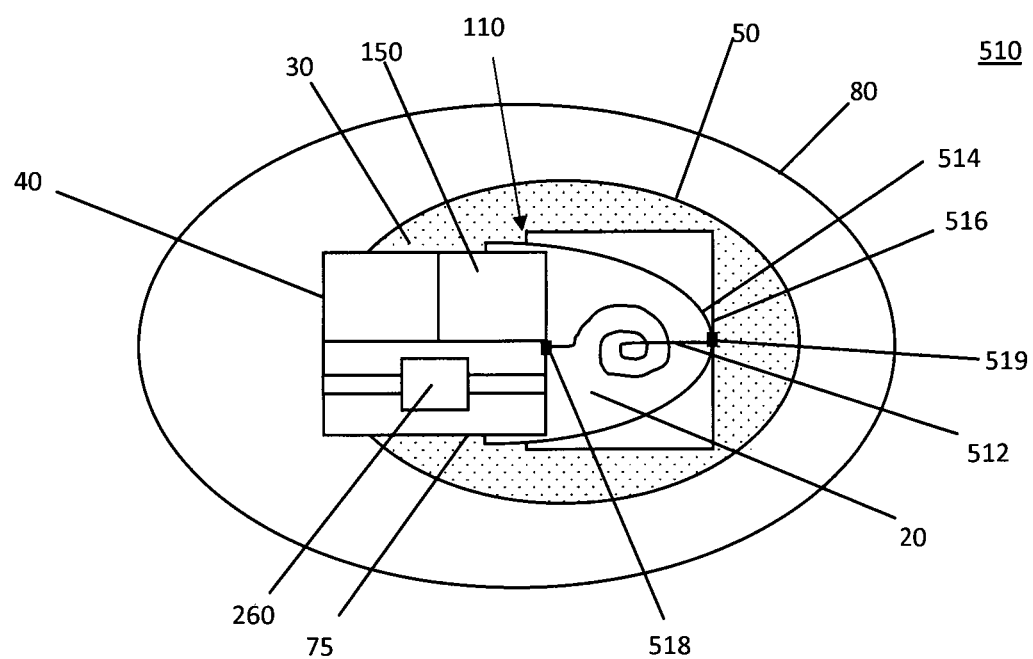
FIG. 12 shows a cross-sectional view of an embodiment wherein the electrical activator includes a heating point, biasing member, a cover and a separator.

FIG. 12 shows an embodiment wherein the electrical activator 110 includes a biasing member 512, a separator 514, a cover 516 and a heating point 518.

The first substance 20 is stored between the casing 75 and the separator 514 and the second substance 30 is stored within the balloon 50 and thereby prevented from mixing with the first substance 20 by the separator 514. The normally closed valve 260 is located in the casing 75 for controlling the release of the gas 22 (not shown) during the deflation of the balloon 50. The separator 514 may be a membrane.

The biasing member 512 may be a compressible coil that is held in torsioned or coiled between the casing 75 and the cover 516 at each of the two ends of the coil. At one end where the biasing member 512 is attached to the casing 75 is the heating point 518 and at the other end where the biasing member 512 is attached to the cover 516 is a coil support 519. The cover 516 is press-fitted on the casing 75 via the separator 514 and a portion of the separator 514 is attached to the cover 516 at the coil support 519.

The dissolvable substance 80 dissolves when it contacts the stomach acid, hence allowing the balloon to inflate.

Figure 13:
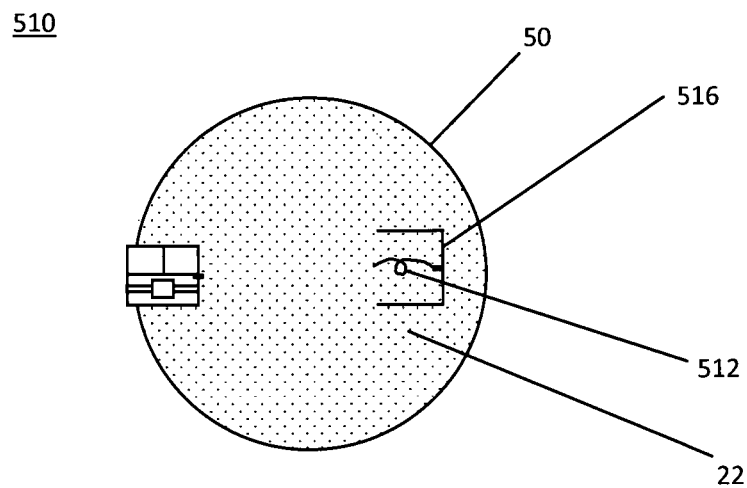
FIG. 13 shows a cross-sectional view of the embodiment in FIG. 12 after the balloon has been inflated.

FIG. 13 shows the embodiment in FIG. 12 after the balloon 50 has been inflated. Although it is not shown in FIG. 12, the receiver (not shown) may be incorporated in the design to allow remote control. Upon receiving a control signal, the receiver sends the control signal to the controller 150 and the controller 150 activates heating point 518. The heating point 518 generates thermal energy and heats the biasing member 512 and when the surrounding temperature of the biasing member 512 meets the melting point of the member 512, the biasing member 512, where it is attached to the casing 75, melts and an impulse tension causes the biasing member 512 to be released from its torsioned state and springs away from the casing 75. The spring effect of the biasing member 512 forces the cover 516 to extend linearly outwards away from the casing 75 and pulls and releases the separator 514 along thus allowing the first substance 20 to contact the second substance 30 and react. From the reaction, the gas 22 is generated and inflates the balloon 50 as in the previous embodiments. The maximum volume of the balloon 50 is achieved when first substance 20 has fully reacted with the second substance 30.

Once the desired duration of treatment is reached, the balloon 50 is deflated to allow the device 510 to be expelled from the user's stomach S. The method of deflation is as per the previous embodiments via valve 260.

Figure 14A:
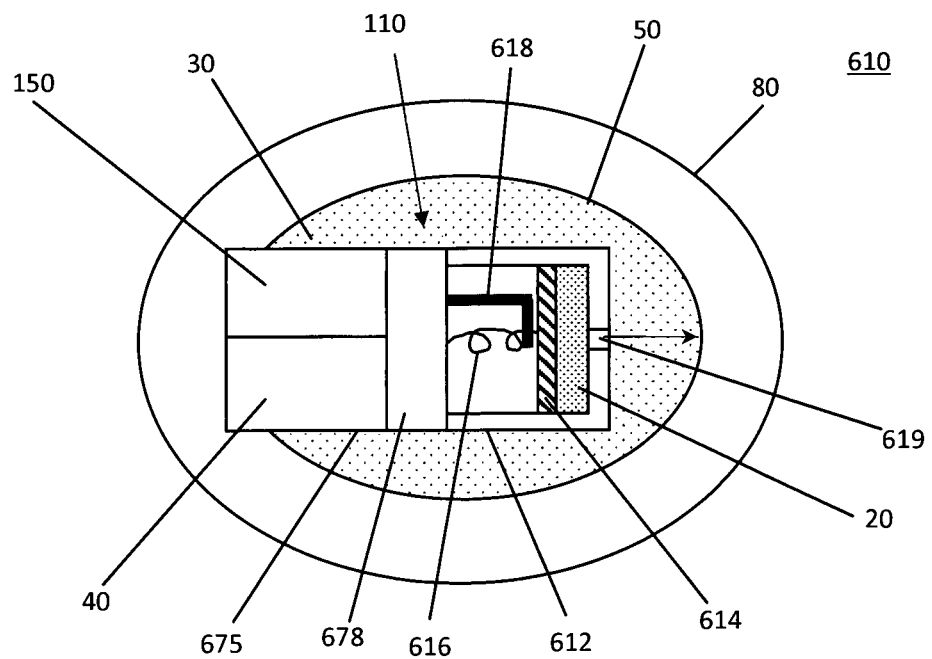
FIG. 14A shows a cross-sectional view of an embodiment wherein the electrical activator includes a plunger, resilient member, a syringe and a stopper.

FIG. 14A shows an embodiment wherein the electrical activator 110 includes a syringe 612 having a plunger 614, a resilient member 616 and a stopper 618. In the syringe 612 is the first substance 20. The first substance 20 is separated from the second substance 30 by the syringe 612. The second substance 30 surrounds the casing 75 and is within the balloon 50, before activation. The plunger 614 is actuated by resilient member 616 but the resilient member 616 is held in a compressed state by stopper 618. The stopper 618 is supported by a support base 617.

The resilient member 616 may be a spring e.g. a helical spring. The resilient member 616 has to be able to support the plunger 614 and a high bending stiffness to counter rotation of the stopper 618 when releasing the resilient member 616.

At one end of the casing 75 is the normally closed valve 260 for controlling the release of the gas 22 (not shown) during the deflation of the balloon 50.

The dissolvable substance 80 dissolves when it contacts the stomach acid, hence allowing the balloon to inflate.

Figure 14B:
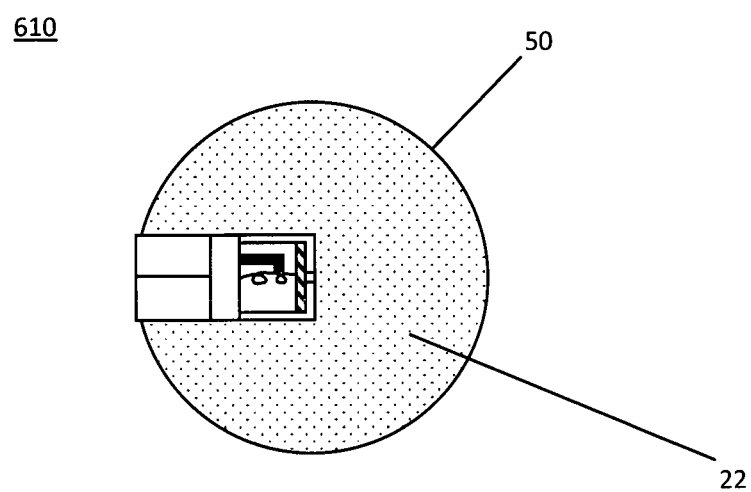
FIG. 14B shows a cross-sectional view of the embodiment in FIG. 14 after the balloon has been inflated.

FIG. 14B shows the embodiment in FIG. 14 after the balloon 50 has been inflated. Upon receiving a control signal, the receiver 160 sends the control signal to the controller 150 and the controller 150 activates the stopper 618 and the stopper 618 rotates or swings away to release the resilient member 616. The released or uncompressed resilient member 616 then drives the plunger 614 along the inner wall of the syringe 612 towards an outlet 619 as shown in FIG. 14A. The plunger 614 forces the first substance 20 out of the syringe 612 and allows the first substance 20 to contact the second substance 30 and react. From the reaction, the gas 22 is generated and inflates the balloon 50. The maximum volume of the balloon 50 is achieved when first substance 20 has fully reacted with the second substance 30.

Once the desired duration of treatment is reached, the balloon 50 is deflated to allow the device 610 to be expelled from the user's stomach S. The gas 22 may be released from the balloon 50 by puncturing it by using a heating coil (not shown). The coil can be at one edge of the balloon 50 and be heated by the command of the controller 150. Once punctured, the gas 22 may escape and collapse the balloon 50 and the deflated device 610 may be removed from the user's body by passing by the lower gastrointestinal tract naturally.

Figure 14C:
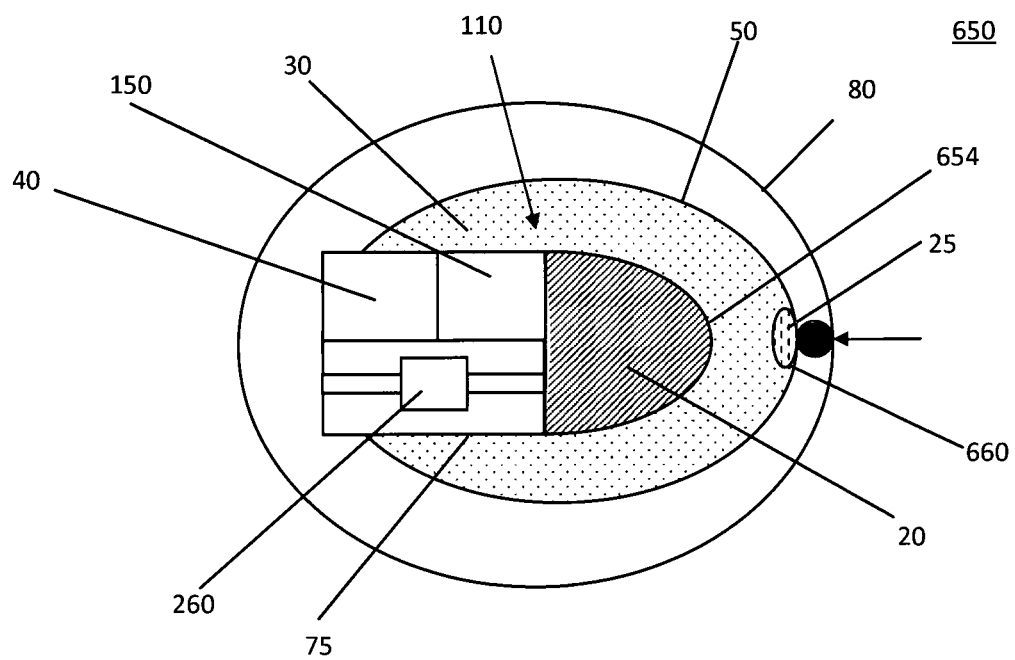
FIG. 14C shows an embodiment of balloon inflating device activated by a compound.

FIG. 14C shows an embodiment of balloon inflating device 650 activated by a compound 25. The compound 25 may be stored in a compartment 660. The first substance 20 is separated from the second substance 30 by separator 654. The second substance 30 surrounds the casing 75 and is within the balloon 50, before activation.

The compartment 660, which may also be referred to as a chemical-release compartment, may be soft and may be made from gelatin. The compartment 660 is distinctively positioned on the dissolvable substance 80 so that the user is able to press on it using fingers easily (see arrow) to break the compartment 660 and release the compound 25 before swallowing as the soft compartment would break under mechanical force. The compartment 660 may be able to contain compound 25 for a certain period of time.

A time-delay trigger (not shown), controlled by using a time-delay function relay, may be used to deflate the balloon 50. It may be necessary to precisely determine the time to trigger the deflation so as to ensure optimal use of this embodiment.

The separator 654, which may be a chemical-dissolvable barrier membrane.

When the compartment 660 is punctured before swallowing, compound 25 may be released to dissolve the separator 654. When swallowed, the dissolvable substance 80 is dissolved when it contacts the stomach acid, hence allowing the balloon to inflate. When the separator 654 is dissolved, the first substance 20 may exit from the separator and contact the second substance 30. The reaction between the first substance 20 and the second substance 30 may take place and generate gas 22.

Figure 14D:
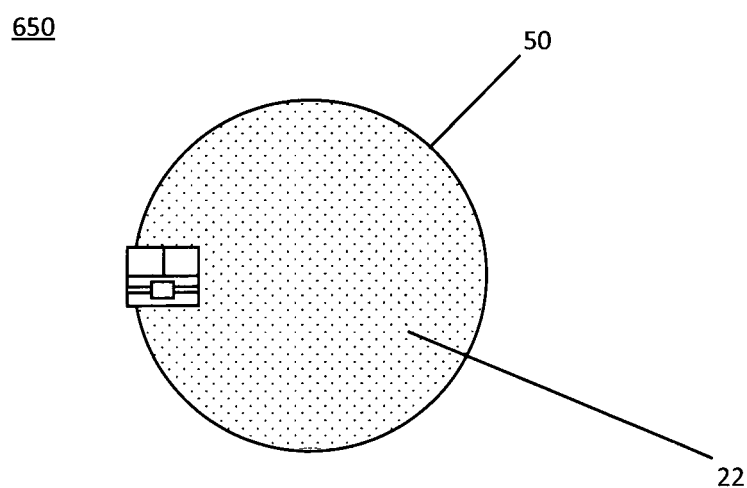
FIG. 14D shows the embodiment in FIG. 14 after the balloon 50 has been inflated.

FIG. 14D shows the embodiment in FIG. 14C after the balloon 50 has been inflated. From the reaction, the gas 22 is generated and inflates the balloon 50. The maximum volume of the balloon 50 is achieved when first substance 20 has fully reacted with the second substance 30.

Once the set time is up, the time-relay trigger may break the balloon 50 to deflate it to allow the device 650 to be expelled from the user's stomach S. Once punctured, the gas 22 may escape and collapse the balloon 50 and the deflated device 610 may be removed from the user's body by passing by the lower gastrointestinal tract naturally.

Apart from the use of the device for weight management, the device may also be used to unclog a constricted portion of the digestive tract.

Figure 15:
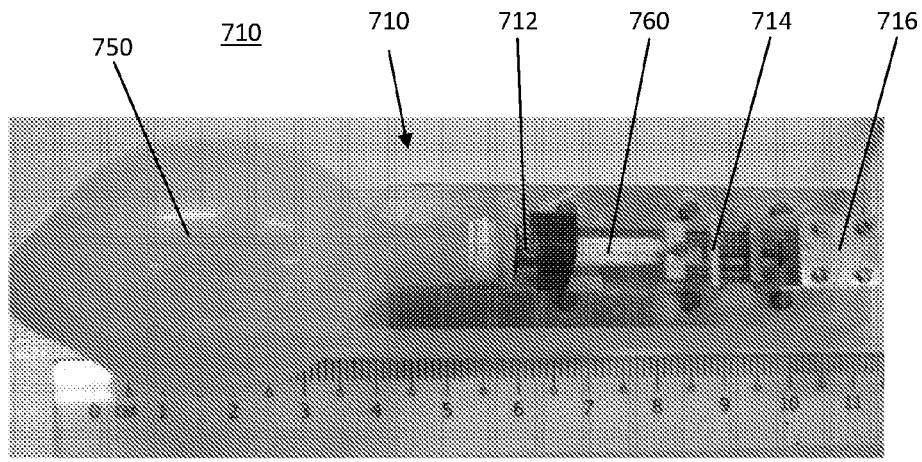
FIG. 15 shows a pictorial view of an embodiment of balloon inflating device with an inflated balloon.

FIG. 15 shows an embodiment of balloon inflating device 710 with an inflated balloon 750. According to various embodiments, the device 710 is activated by a plunger 714 and an actuator 716 combination. The plunger 714 is part of a syringe 712 which contains a first substance 720 and the balloon 750 contains a second substance 730 and it is attached to the syringe 712. When the plunger 714 is pushed towards the balloon 750 by the actuator 714, the first substance 720 is pushed out of the syringe 712 and into the balloon 750 and contacts the second substance 730. When contacted, the first substance 720 and second substance 730 reacts to generate a gas 722 to inflate the balloon 750. According to various embodiments, the dimension of the small actuator 716 is 3.4 mm in diameter and 22.85 mm in length.

Figure 16:
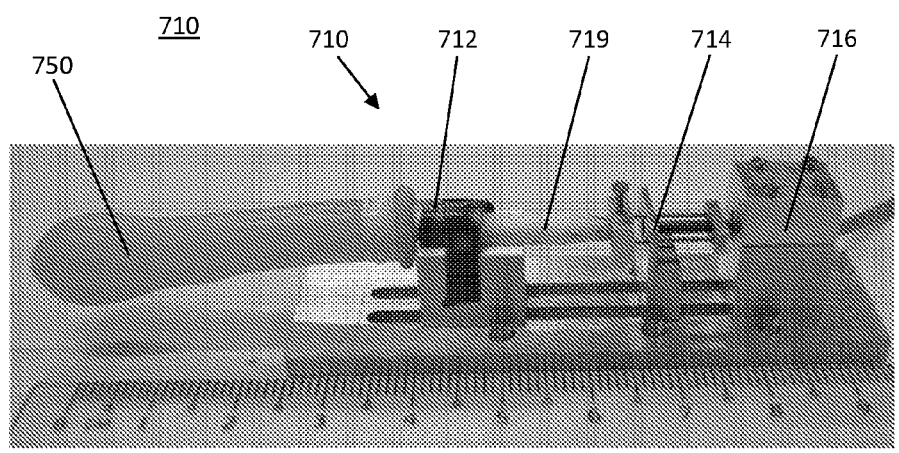
FIG. 16 shows a pictorial view of the embodiment in FIG. 15 after the balloon has been deflated.

FIG. 16 shows the embodiment in FIG. 15 after the balloon 750 has been deflated. To deflate the balloon 750, the actuator 716 pulls back the plunger 714 so that the gas, driven by the pressure difference, can escape through the deflation outlet 760.

According to various embodiments, the first substance 720 includes 0.1 ml Acetic Acid of 80% concentration and the second substance 730 includes 1 gram of Sodium Bicarbonate. When the actuator 716 pushes the plunger 714, reaction takes place and the balloon 750 is inflated to approximately 30 ml. In order to get a bigger volume, the amount of the substances may be increased. As shown in the embodiment, the inflation and deflation of balloon 750 can be carried out without any external intervention.

Figure 17:
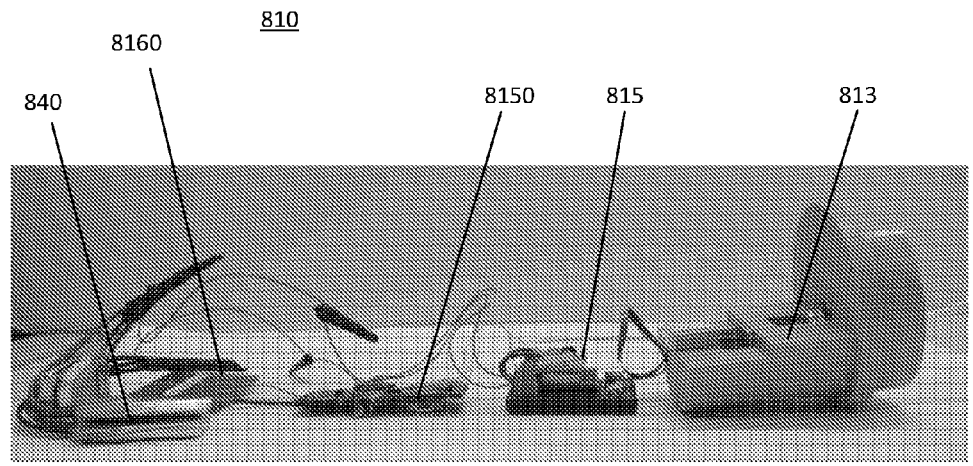
FIG. 17 shows a pictorial view of components of an embodiment of a balloon inflating device.

FIG. 17 shows components of an embodiment of a balloon inflating device. The embodiment is integrated with a receiver 8160 into the previous embodiment. As shown in FIG. 17, the device 810 includes an actuator hub 813, an actuator driver 815, a controller 8150, a receiver 8160 and a power supply 840. The components are meant to be assembled in a casing (not shown).

The actuator hub 813 includes an actuator (not shown) and is capable of inflating and deflating a balloon (not shown). The hub 813 is made of Polyetheretherketone (PEEK) plastic material.

The actuator driver 815 includes a speed controller card capable of controlling the actuator 816 by passing pulse width modulated power signal to it. According to various embodiments, the card may be Faulhaber SC1801F.

The actuator 816 includes a mini brushless dc motor coupled with a fine thread (1.6 mm in diameter and 0.20 mm pitch) lead screw.

A syringe (not shown) having a 5 ml capacity is used in the embodiment. The syringe 812 has a tube extended from its tip for fluid communication between the syringe 812 and the outside of the casing 875 to allow the flow of the first substance 820 from within the syringe 812 to contact the second substance 830.

The controller 8150 includes of a micro controller (Texas instrument MSP430F1611) and a transceiver (Zarlink ZL70101 402-405 MHz MICS (Medical Implantable Communications Service) band). The transceiver is connected to an antenna.

The power supply 840 used in this embodiment is a Lithium-ion battery, which outputs a nominal 3.7V at 100 mAh.

Figure 18:
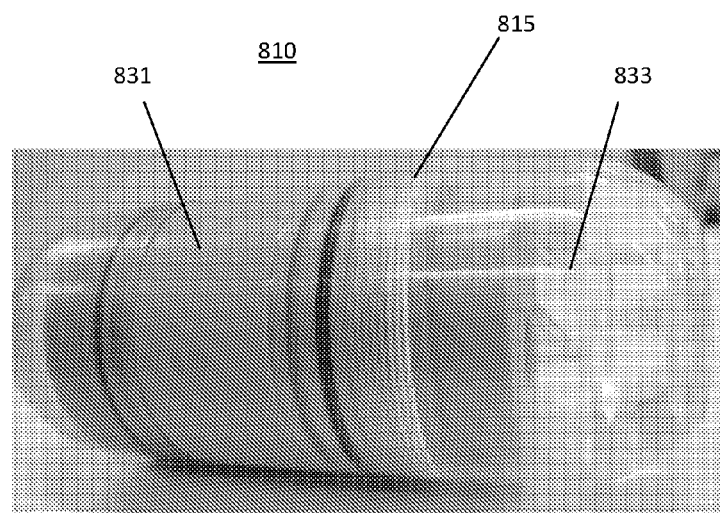
FIG. 18 shows a pictorial view of a casing of the assembled embodiment in FIG. 17.

FIG. 18 shows a casing of the embodiment in FIG. 17 which includes a first portion 831 made of PEEK and a second transparent portion 833 made of thermoplastic (PMMA). According to various embodiments, the casing 875 has a dimension of 58 mm in diameter and 157 mm in length.

According to various embodiments, the first substance 820 includes 0.9 ml of 80% concentration of Acetic Acid and the second substance 830 includes 5 grams of Sodium Bicarbonate diluted in 10 ml of distilled water. This chemical combination may inflate the balloon 850 to about 200 ml.

The balloon 850 is made of natural latex balloon, with thickness of 0.08 mm.

Figure 19:
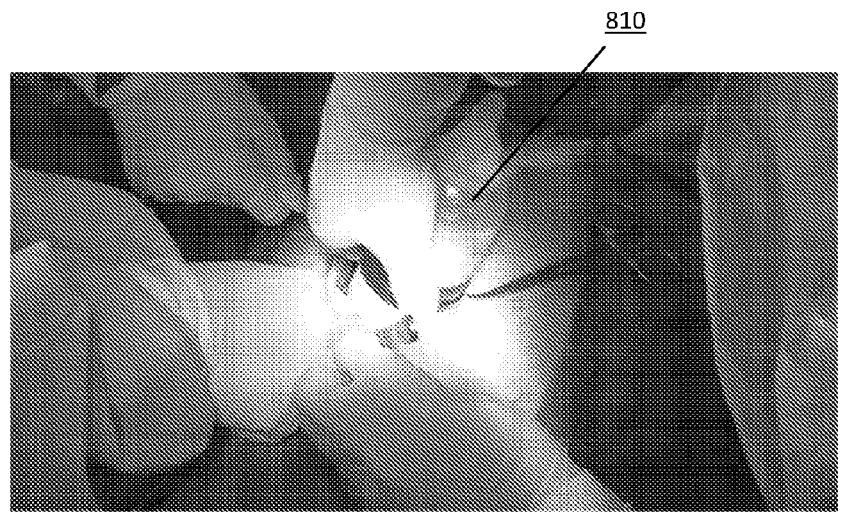
FIG. 19 shows a pictorial view of the embodiment in FIG. 18 when in use.

FIG. 19 shows the embodiment in FIG. 18 being tested on an animal. The capsule was inserted through gastronomy.

Figure 20:
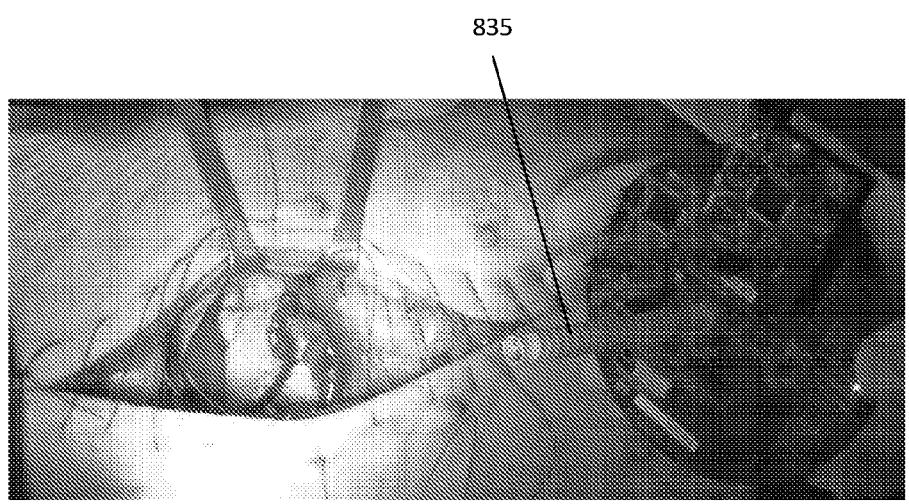
FIG. 20 shows another pictorial view of the embodiment in FIG. 18 when in use.

FIG. 20 shows the embodiment in FIG. 18 after being inserting into the animal. After the insertion of the embodiment, an antenna 835 was placed near to the stomach in order to test the strength of a signal transmission as shown in FIG. 20. Once the signal transmission was established, the stomach was sutured layer by layer in order to close the incision on the stomach and prevent air leakage. The antenna 835 was connected to a laptop (not shown) installed with the graphical user interface (GUI) of the Zarlink communication module.

Figure 21:
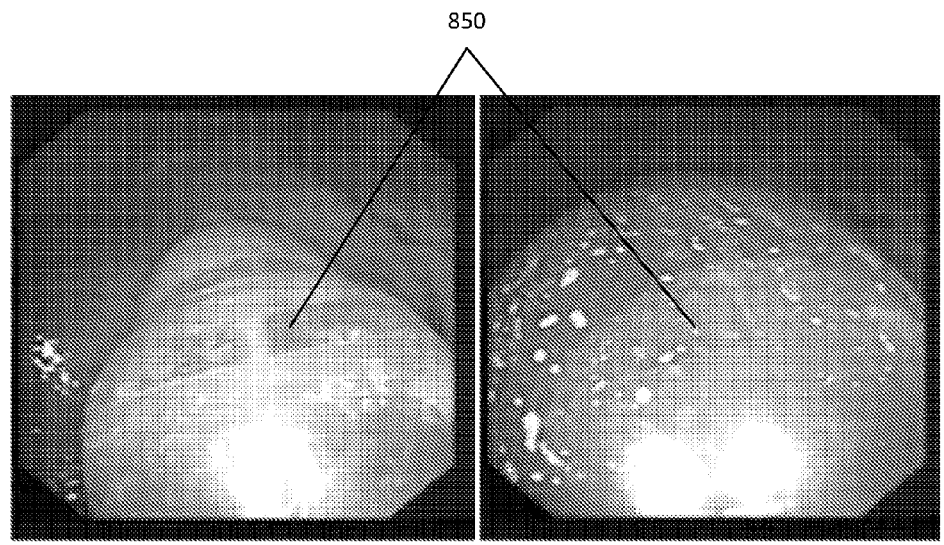
FIG. 21 shows an endoscopic view of the embodiment in FIG. 18 when in use.

FIG. 21 shows the embodiment with inflated balloon in the animal. Another visual aid was introduced by inserting an endoscope into the stomach cavity in order to observe the device performance. From the endoscopic view, the vision of the embodiment may be observed. In FIG. 21, it is shown that the endoscope captured the images of the balloon 850 before and after the inflation. The inflation was initiated when a user activated the signal transmission through the GUI. As described previously, once the transceiver received the signal, the actuator 816 is powered to push the plunger 814 and the gas generating reaction takes place. In this experiment, it is shown that the device could perform balloon inflation via the radio transmission.

Figure 22:
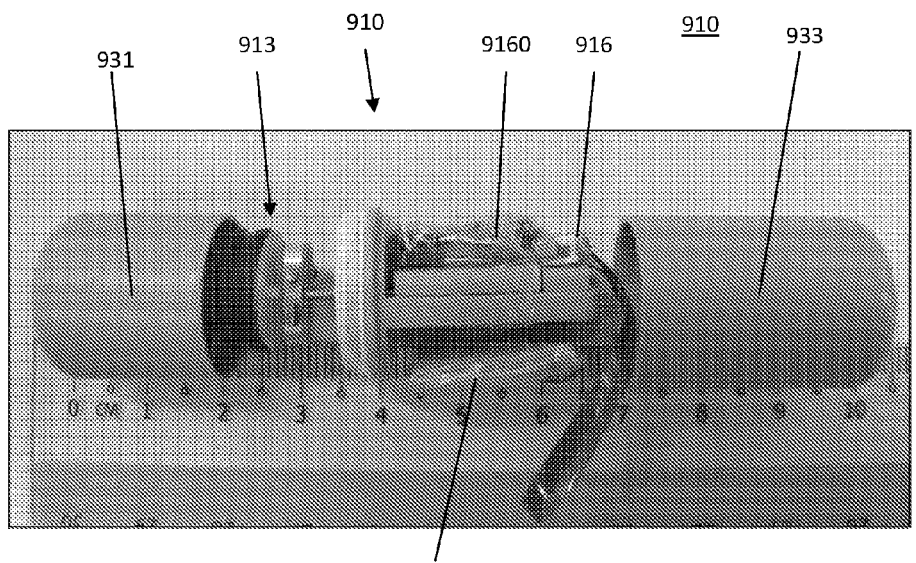
FIG. 22 shows a pictorial view of the components assembled in an embodiment.

FIG. 22 shows the components assembled in an embodiment. The device 910 has a casing 975 includes a first portion 931 and a second portion 933. The casing 975 houses a syringe assembly 913, a power supply 940 and a communication system 9160. The first portion 931 encloses a syringe assembly 913 and the second portion 933 encloses the lower half of the casing 975. The casing 975 is to be inserted into a balloon (not shown). The device 910 also has a controller 9150 for receiving any control signal and activating the inflation of the balloon 950.

The power supply 940 may be a battery and may provide electricity to the communication system 9160.

The communication system 9160 may provide the response data, and activates an actuator 916 which may be a linear motor.

After the casing 975 is inserted into the balloon 950, part of it may be tied to the balloon 950. According to various embodiments, the casing 975 does not protrude from the balloon 950 i.e. the balloon 950 will cover casing 975 completely. The overall dimension of the casing in the embodiment is 19 mm in diameter and 50 mm in length. The outer part of the casing 975 and an internal support body (not shown) for an actuator 916 may be made of Polyetheretherketone (PEEK).

The syringe assembly 913 includes syringe 912 (not shown) attached to it and has connectors that may be made of aluminum. According to various embodiments, the actuator 916 is placed inside the syringe assembly 913.

The controller 9150 may include a low-power processor and an antenna. The processor in the embodiment may be a low-power sub-1 GHz system-on-chip by Texas Instruments (CC1110Fx/CC1111Fx). The dimensions of the controller 9150 in the embodiment are 23 mm in length, 11 mm in width and 5 mm in height. The processor may include a RF transceiver, and in this embodiment, the processor may be from Texas Instruments (CC1101) and is equipped with an industry-standard enhanced 8051 MCU. The size (small 6×6 mm) of the processor makes it very suited for applications with size limitations.

The power supply 940, which may be a battery, may be of dimensions 20 mm in length, 12 mm in width and 4 mm in height, used in the embodiment is a Polymer Lithium Ion battery, which outputs a nominal 3.7V at 20 mAh.

According to various embodiments, the balloon 950 may be made of a plastic alloy that includes of Polyethylene Terephthalate (PET)—Polyurethane (PU)—Polypropylene (PP) configuration. The balloon 950 may be multi-layered may have an outermost layer and an inner layer. The outermost layer is made of PET and the inner layer is made of PP. The layers are adhered together with PU.

Polypropylene (PP) layer provides additional features to the known PET and PU gas barrier properties. PP polymers are linear polyolefins with the repeating structure of methyl group. In general, PP is semi-rigid in structure and has tough and good fatigue resistance and good heat resistance (heat distortion temperature at 66 psi of 99-127° C.). PP resists stress-cracking and offers electrical and chemical resistance at higher temperatures. As it has good heat resistance property, it would not melt or deform easily. This is important to ensure that the intragastric balloon 950 can withstand a certain amount of force.

Due to the layers of PET and PU, a property of this alloy is that it has both relatively low carbon dioxide permeability and reasonable chemical resistance. Because of PP's structure, it can withstand impact force or pressure, hence reduces the risk of the balloon rupturing. In general, the balloon 950 is not compostable, biodegradable, or photodegradable or made from bio based resins (made from renewable resources—agricultural crops, rather than from petroleum) at this time.

Figure 23A:
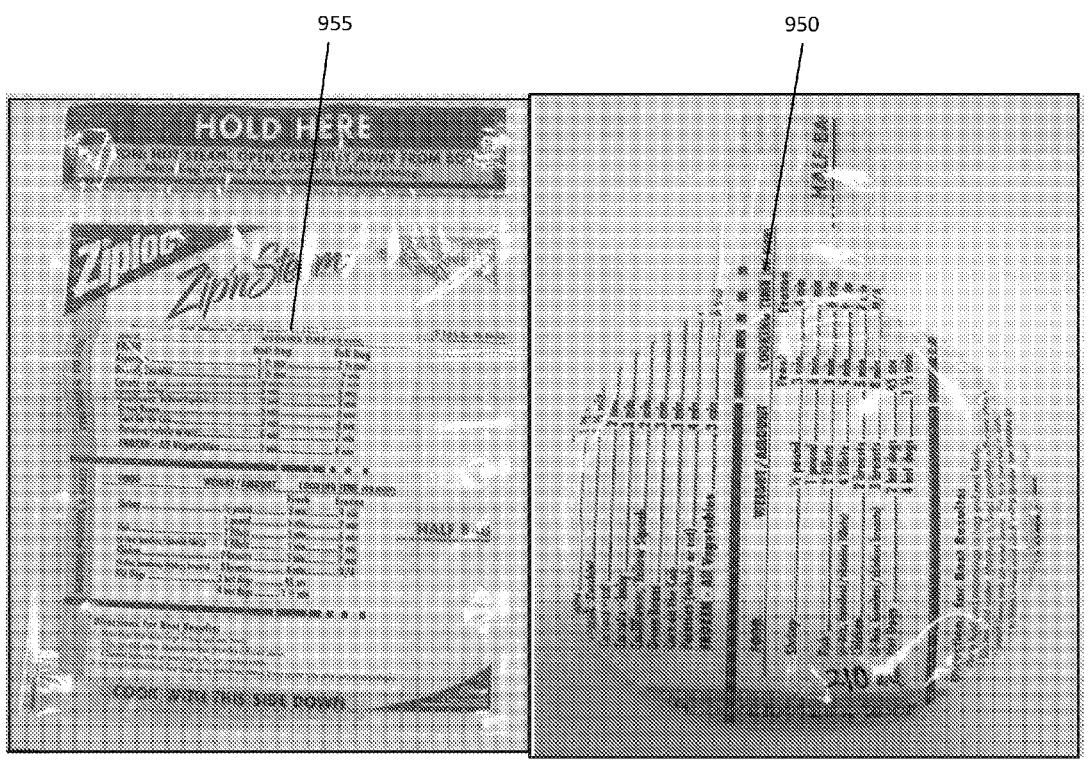
FIG. 23A shows a plastic bag used for the fabrication of balloon and a balloon made from the bag.

FIG. 23A shows a plastic bag 955 used for the fabrication of a balloon 950 and a balloon 950 made from the bag.

Figure 23B:
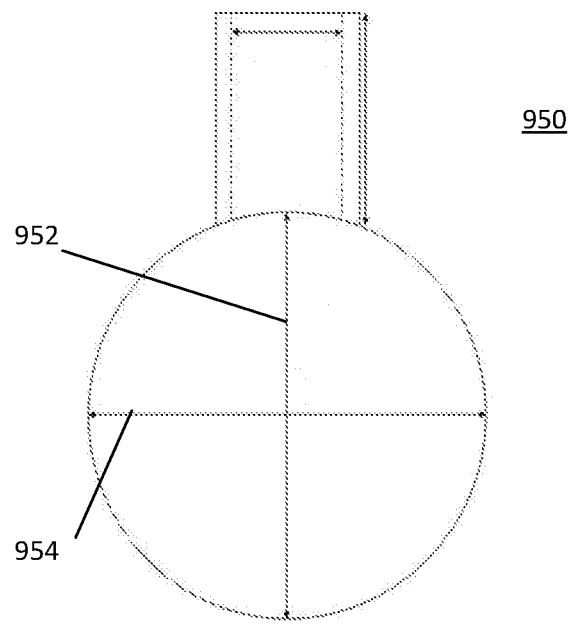
FIG. 23B shows an aspect of the balloon used in the embodiment in FIG. 22.

FIG. 23B shows the dimension of the balloon 950, as applicable to all the embodiments, may be decided based on the overall dimension of the casing 975 and how it is attached to the balloon 950. Another important consideration is the estimated amount of carbon dioxide/water that may be produced e.g. if the fluid would fill up to three quarters of the balloon's spherical volume. The edges of the balloon 950 are rounded and smooth to minimise any abrasion along the gastrointestinal tract thus minimizing any discomfort to the user. An example of the shape of balloon 950 is shown in FIG. 23. The balloon 950 may include an elliptical profile with length of 12.5 cm along its major axis 954 and length of 11 cm along its minor axis 952. The rectangular profile adjacent may have length of 6 cm and width 4.5 cm.

Figure 24:
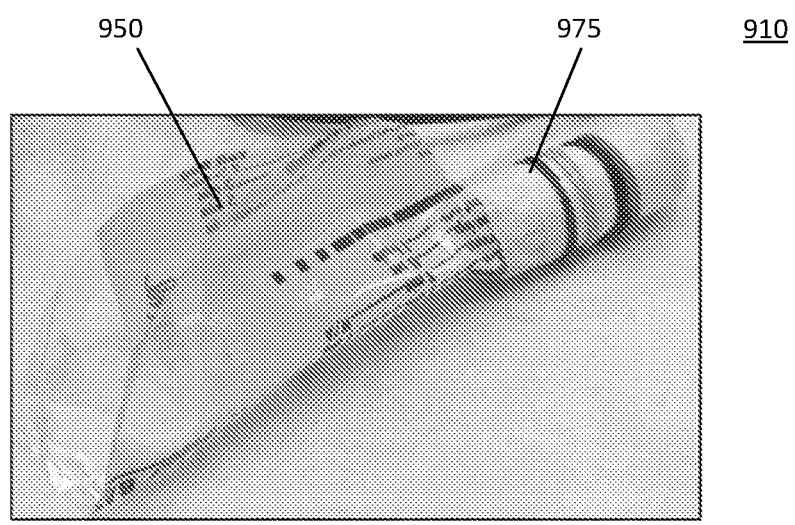
FIG. 24 shows a pictorial view the embodiment in FIG. 22 being inserted into the balloon in FIG. 23.

FIG. 24 shows the embodiment in FIG. 22 being inserted into the balloon in FIG. 23. As shown in FIG. 24, the casing 975 may be inserted into the balloon 950 and they were attached together.

Figure 25:
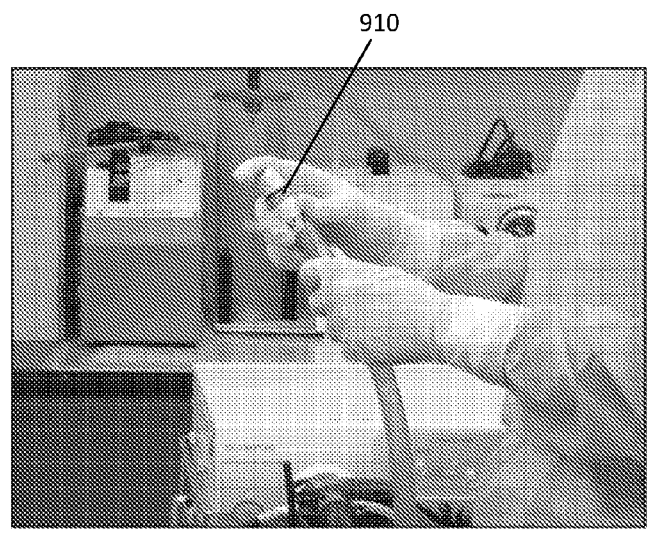
FIG. 25 shows a pictorial view of the embodiment in FIG. 22 when in use.

FIG. 25 shows the embodiment in FIG. 24 being inserted into a tube. The embodiment was put to trial and the casing 975 was inserted into the stomach of an animal through its mouth using the tube. To do so, the casing 975 was inserted into a tube and lubricating gel was applied onto the balloon 950 and the tube to allow a smooth entry of the casing 975 into the animal. The casing 975 was inserted into the animal's stomach through its mouth. The insertion process was captured endoscopically. After the insertion, an antenna was placed near to the stomach to test for a signal transmission. The antenna was connected to a laptop installed with a customized graphical user interface (GUI) developed in-house. A two-way communication is maintained and status information of the device 910 can be observed on the laptop.

According to various embodiments, the first substance 920 includes 0.7 ml of 80% concentration of Acetic Acid and the second substance 930 includes 1 grams of Sodium Bicarbonate diluted in 2 ml of distilled water. This chemical combination may inflate the balloon to about 110 ml.

Once the signal transmission was established, a remote control signal was sent to the communication system 9160 which in turn transmitted the signal to the controller 9150. The controller 9150 then activates the actuator 916 to push the first substance 920 out of the syringe 912 to contact the second substance 930. The substances react upon contact and generate gas 922 to inflate balloon 950.

Figure 26:
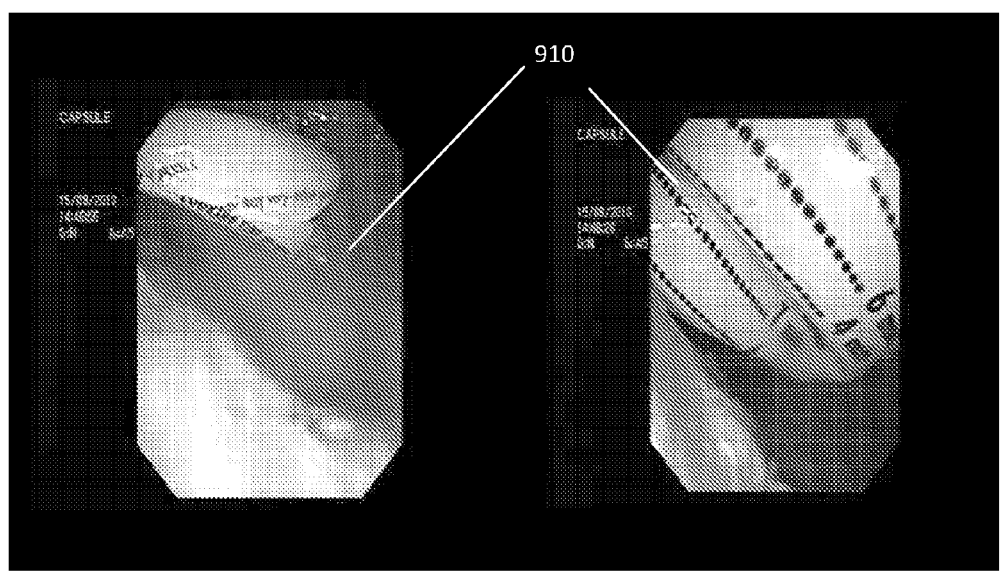
FIG. 26 shows an endoscopic view of the embodiment in FIG. 22 before and after inflation when in use.

FIG. 26 shows an endoscopic view of the balloon 950 before and after inflation.

Figure 27:
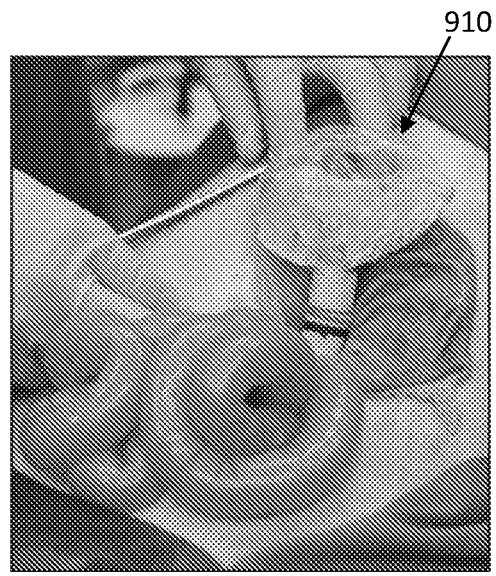
FIG. 27 shows another pictorial view of the embodiment in FIG. 22 when in use.

FIG. 27 shows the embodiment of FIG. 24 being removed from the animal. The casing 975 was left in the animal's stomach for about a week. After the week, the embodiment was removed for testing and the condition of the animal was checked. As shown in FIG. 27, an incision was made to the animal's stomach and the embodiment was retrieved from the stomach.

Figure 28:
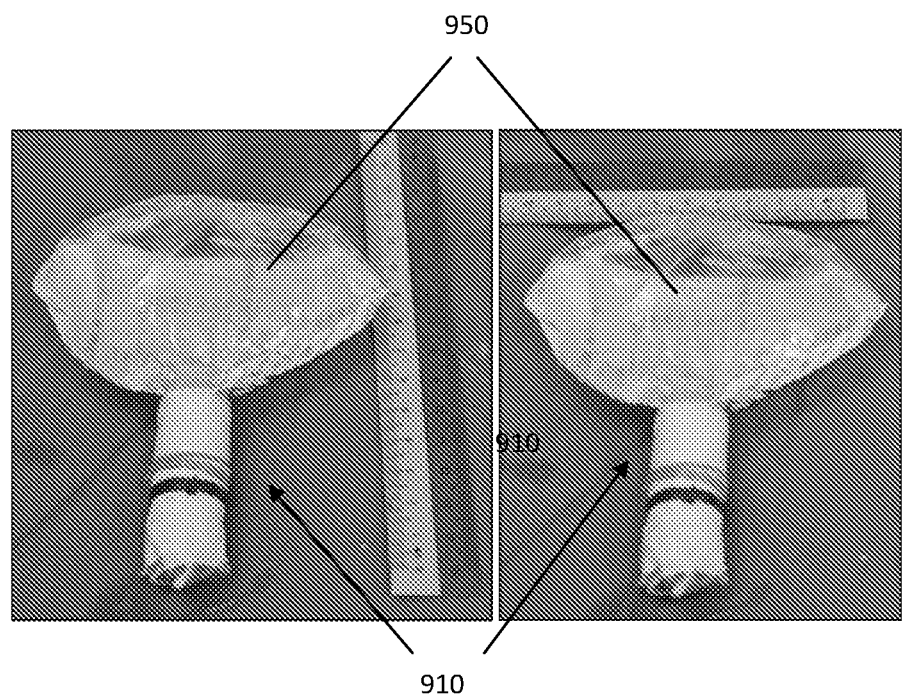
FIG. 28 shows a pictorial view of the embodiment in FIG. 27.

FIG. 28 shows the retrieved balloon 950 and an estimate of the dimensions. As shown in FIG. 28, the balloon 950 remains inflated and intact to the casing. In addition, the balloon 950 was not damaged by the high concentration of hydrochloric acid in the stomach cause. Even if there is any leakage, the carbon dioxide and water leaked are non-toxic to the user's body. It is therefore shown that the device 910 is feasible in this trial.

Using a linear motor as an actuator provides the ability to control the amount of first substance 920 i.e. acetic acid released and hence the control on the estimated volume of gas 922 i.e. carbon dioxide/water generated.

Although some of the previous embodiments showed the use of a valve to release the gas from the balloon, there are other possibilities that may be contemplated in the release of the gas from the balloon.

Figure 29:
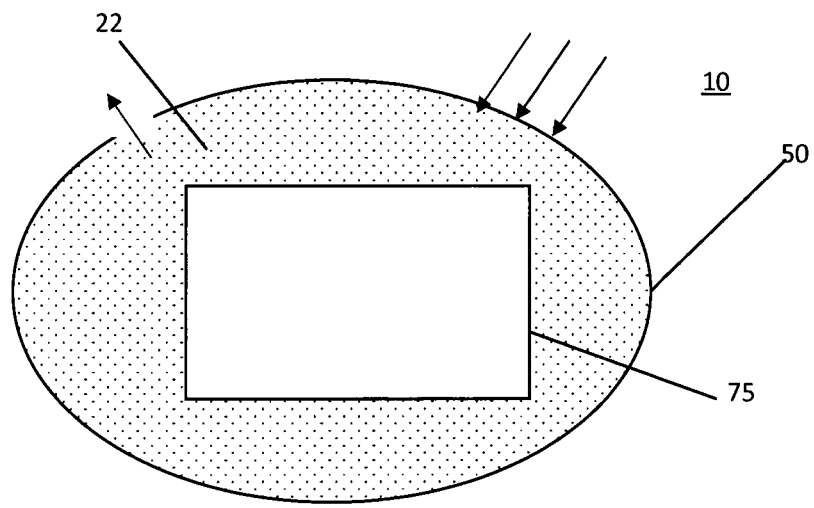
FIG. 29 shows a punctured balloon due to degeneration of balloon material.

FIG. 29 shows a punctured balloon 50 due to degeneration of balloon material. The balloon material may be chosen to be susceptible to degenerate when in contact with strong hydrochloric acid, e.g. the hydrochloric acid in the stomach can completely degenerate the balloon 50. The degeneration will eventually cause a puncture in the balloon 50 and the gas 22 leaks from the puncture. When the balloon 50 is completely degenerated in the stomach, the gas would have all entered the stomach. Finally the deflated system will be removed from the user body by passing through the lower gastrointestinal tract naturally.

Figure 30:
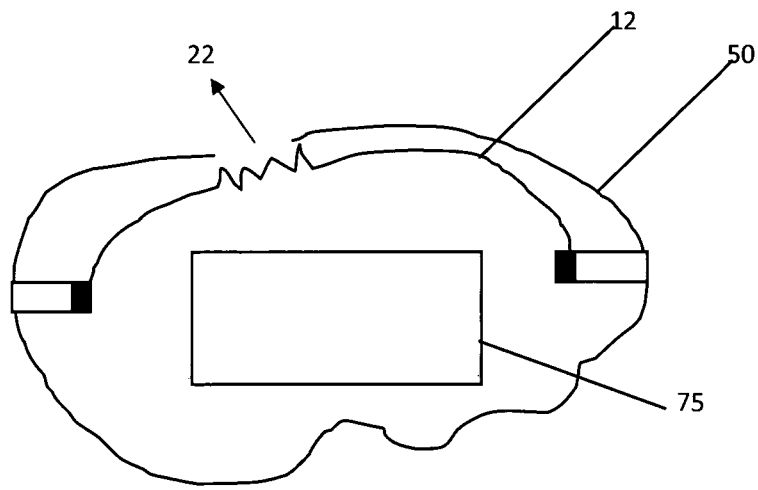
FIG. 30 shows a punctured balloon due to a heating coil.

FIG. 30 shows a punctured balloon 50 due to a heating coil 12. The heating coil 12 may be used to puncture the balloon 50 by placing the coil at one edge of the balloon 50. The heating coil is controlled by the controller and electricity to heat the coil is supplied by the power supply.

Figure 31:
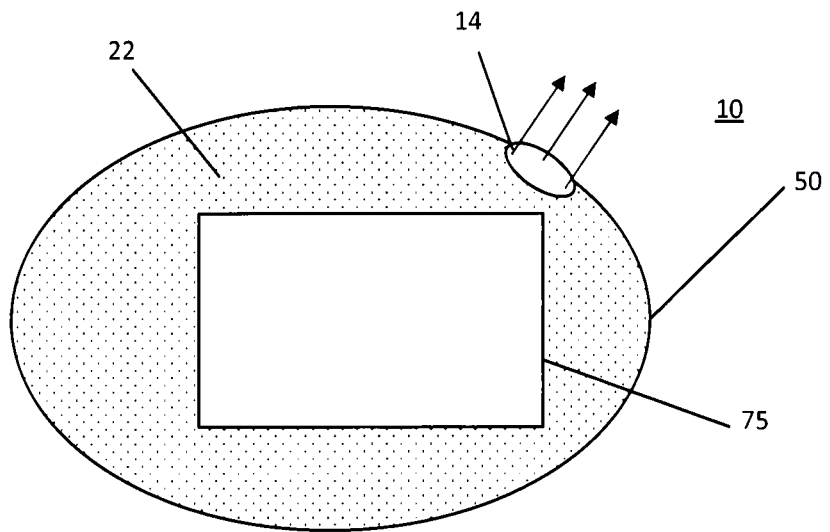
FIG. 31 shows a punctured balloon due to a time delay trigger.

FIG. 31 shows a punctured balloon 50 due to a time delay trigger 14. Apart from using the controller to control the deflating of the balloon 50, a time delay trigger 14 (controlled by using a time-delay function relay) can be used to break the balloon 50 to let the gas escape (see arrows) from the balloon 50 into the external environment (i.e. stomach cavity).

Figure 32:
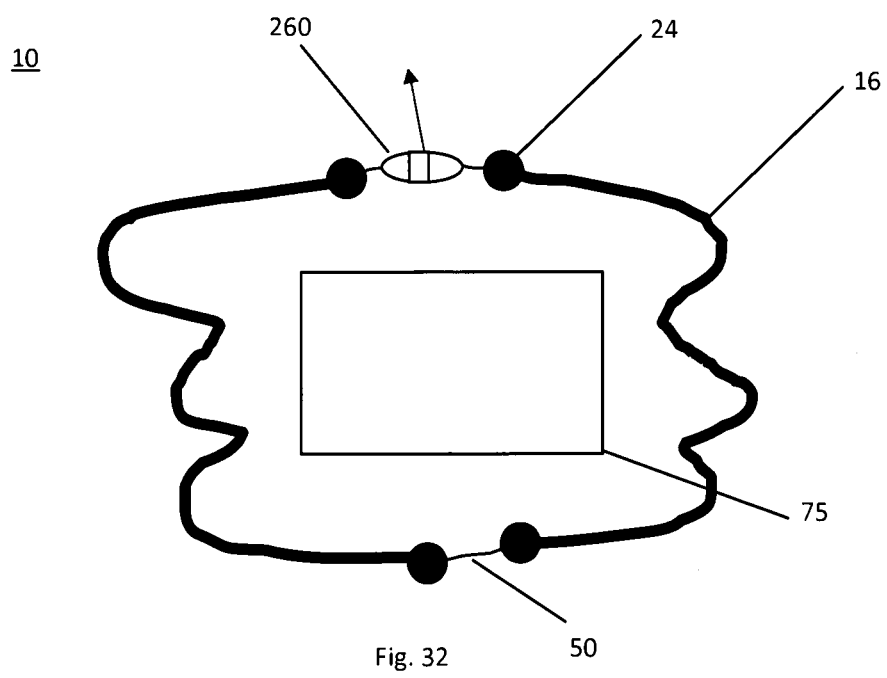
FIG. 32 shows a deflated balloon with shape memory alloy.

FIG. 32 shows a deflated balloon 50 with shape memory alloy 16. When the balloon 50 is deflated, it may not contract to its original shape due to the degeneration of the material. To aid the contraction to substantially its original shape, shape memory alloy 16 (which may be also be referred to as "smart memory alloy") may be used. The shape memory alloy is an alloy that "remembers" its original, cold-forged shape and can be returned to its pre-deformed shape by heating. The shape memory alloy is in thermal contact with a heat source 24 (relay control from the heating source). When the balloon 50 inflates and distorts the shape memory alloy 16 from its original shape, heat can be applied to return the alloy to its original shape thus contracting the balloon 50 to substantially its original size and/or shape. This also allows the gas 22 to be substantially squeezed from the balloon 50 and be as close to the casing 75 as possible. According to various embodiments with a valve arrangement 260, the pressure exerted by the alloy may be higher than the maximum pressure that the valve can withhold. This may cause the valve to open and allow the gas to escape.

The device may be equipped with mechatronics components, on-board sensors and two-way wireless communication means to allow a closed loop system between the casing and an external control system. With an operator controlling the external system, the device may be fully controlled. There may be sets of sensors and actuators (e.g. mechatronics devices, chemical components) integrated into the device, and the external system will always receive detailed information of the surrounding environment of the device (e.g. location, temperature, humidity, pH, pressure, etc). In addition, sensors equipped into the device include temperature, pressure and pH sensors. These additional sensors may allow the device to be inflated or deflated at the precise timing and location.

Elastomers such as rubber may be considered for the balloon. Natural rubber, which is commonly seen in the daily life, is bio-compatible and it is also a material with excellent elasticity. However, it was not possible for rubber to retain the carbon dioxide. This is mainly due to characteristics of the polymer chains of the rubber. To possess good elasticity, the connections of chains or the crystallinity of the material is at a very low level and materials with low crystallinity provide free spaces that may allow carbon dioxide gas molecules to move through and escape through the balloon, which may result in substantial gas leakage.

Plastic has higher crystallinity (due to a more densely packed crystal lattice) and tightly-bonded polymer chains (especially in films), which leads to their inherent permeability to low molecular weight substances, including permanent gases, water and organic vapours. There are advanced composite plastic films that are specifically designed and made to exhibit high gas barrier properties, especially in the food package industry. Such materials include Low-Density Polyethylene (LDPE), Polyvinylidene Chloride (PVDC), Polyethylene Terephthalate (PET), Ethylene Vinyl Alcohol (EVOH) and Polyurethane (PU). Not only are they able to contain carbon dioxide, they also have been proven to be non-toxic and bio compatible.

Low-Density Polyethylene (LDPE) is a thermoplastic made from petroleum. It is not reactive at room temperatures, except when in contact with strong oxidizing agents. It can withstand temperatures of 80° C. continuously and 95° C. for a short time. It has a translucent or opaque variation and though quite flexible and tough, it may be breakable. LDPE has more branching (on about 2% of the carbon atoms) than High Density Polyethylene (HDPE), so its intermolecular forces (instantaneous-dipole induced-dipole attraction) are weaker, therefore, its tensile strength is lower, and its resilience is higher.

Polyvinylidene Chloride (PVDC) is a barrier material with high toughness and low hot sealing temperature, heat shrinking ability and chemical stability. It is an ideal packaging material in medicine, food packaging, military packaging industry, especially for its uniqueness in resistance to oxygen, moisture, acid, alkali and various chemical solvents. Because of the strong molecules force and high crystallinity, along with the hydrophobic chlorine atoms in PVDC, it makes oxygen and water molecules difficult to move. PVDC can be applied as a water-based coating to other plastic films such as Biaxial-Oriented Polypropylene (BOPP) and Polyethylene Terephthalate (PET). This coating increases the barrier properties, hence reducing the permeability of the film to oxygen and carbon dioxide.

Polyethylene Terephthalate (PET) is a thermoplastic polymer resin of the polyester family. PET has good mechanical properties and displays excellent resistance to oxygen, carbon dioxide, water, oil, dilute acids, fatty dilute alkali, and most solvents. It also exhibits excellent resistance to high and low temperature performance (i.e. can be in 120° C. temperature range for both long-term and short-term usage). In particular, its permeability to carbon dioxide at 25° C. ranges from 0.07 to 0.11 10-13 cm3·cm·cm-2·s-1·Pa-1. PET is widely used in the beverage package industry for bottling beverages, such as mineral water and carbonated soft drinks.

Current medical applications of PET include implantable sutures, surgical mesh, vascular grafts, and sewing cuffs for heart valves and components for percutaneous access devices.

Ethylene Vinyl Alcohol (EVOH) is a copolymer of Ethylene and Vinyl Alcohol. It is designed and made to provide barrier properties (primarily to oxygen and flavour) for advanced food packaging and also as a hydrocarbon barrier for fuel tanks. EVOH is typically coextruded or laminated as a thin layer between cardboard, foil, or other plastics. EVOH copolymer is defined by the mole percentage Ethylene content; lower Ethylene content grades have higher barrier properties; higher Ethylene content grades have lower temperatures for extrusion. EVOH barrier performance depends on the content of Ethylene. Generally, higher concentration of Ethylene means better gas barrier property, but may be more difficult to machine and fabricate.

Polyurethane (PU) is a polymer which consists of a chain of organic units joined by urethane (carbamate) links. It is produced by reacting diisocyanates with glycols. It can be easily stretched. PU is not easily damaged by chemicals including solvents, acids, and oils. It is often used as transparent barrier film packaging as well as a food adhesive. Their relatively low molecular weight/small molecule size allows them to permeate porous substrates.

The invention claimed is:

1. An intragastric balloon system comprising:
a swallowable device comprising:
an elastic balloon;
a first substance within the balloon;
a second substance within the balloon capable of reacting with the first substance within the balloon to generate a gas to inflate the balloon;
a casing attached to or disposed within the balloon, the casing carrying a passage through which the gas can flow from the interior of the balloon to an environment external to the casing;
a battery disposed within the casing;
a microcontroller disposed within the casing and coupled to the battery; and
an electrical activator carried by the casing, the electrical activator controllable by the microcontroller;
wherein the electrical activator comprises a syringe having a plunger and an actuator configured to drive the plunger, wherein the syringe contains the first substance and the actuator is configured to, when activated electrically, drive the plunger forward and actuate the first substance to contact the second substance to generate the gas, and
wherein the syringe carries an opening connecting to the passage to transfer the gas to the environment external to the casing and the opening is exposed to the generated gas by retracting the forwardly driven plunger backward to deflate the elastic balloon inflated by the generated gas.

2. The system of claim 1, wherein the actuator comprises a stopper and a resilient member held compressed by the stopper and the stopper is configured to, when activated electrically, release the resilient member to drive the plunger.

3. The system of claim 1, wherein the swallowable device further comprises a communication hub disposed within the casing and coupled to the microcontroller, the communication hub configured to receive a remote signal and communicate the remote signal to the microcontroller.

4. The system of claim 1, wherein the swallowable device further comprises a dissolvable coating coated onto the balloon to retain the balloon in a compressed configuration.

5. The system of claim 1, wherein the balloon comprises a heat source and a shape memory alloy in thermal contact with the heat source configured to distort with the balloon from an original shape when the balloon is inflated, wherein the balloon is returned to the original shape when the shape memory alloy is heated.

6. The system of claim 1, wherein the balloon comprises a multi-layered membrane including a plastic film and a layer of rubber.

7. The system of claim 1, wherein the swallowable device further comprises at least one of a temperature sensor, a humidity sensor, an acidity sensor, a pressure sensor, and a positioning sensor.

8. The system of claim 1, wherein the first substance is an acid in an aqueous solution and the second substance is a bicarbonate.

9. The system of claim 1, wherein the balloon comprises a radio-opaque substance.

10. A method for controlling inflation and deflation of a set of swallowable balloons, the method comprising:
providing a swallowable device within a subject's body, the first swallowable device comprising:
an elastic balloon;
a first substance within the balloon;
a second substance within the balloon capable of reacting with the first substance to generate a gas to inflate the balloon;
a casing attached to or disposed within the balloon, the casing carrying a passage through which the gas can flow from the interior of the balloon to an environment external to the casing;
a battery disposed within the casing;
a microcontroller disposed within the casing and coupled to the battery; and
an electrical activator carried by the casing, the electrical activator controllable by the microcontroller,
wherein the electrical activator comprises a syringe having a plunger and an actuator configured to drive the plunger, wherein the syringe contains the first substance, and the actuator is configured to, when activated electrically, drive the plunger forward and actuate the first substance to contact the second substance to generate the gas, and
wherein the syringe carries an opening connecting to the passage to transfer the gas to the environment external to the casing and the opening is exposed to the generated gas by retracting the forwardly driven plunger backward to deflate the elastic balloon inflated by the generated gas;
receiving a remotely generated inflation signal directed to the first swallowable device; and
activating the electrical activator in response to the inflation signal to cause the first substance and the second substance to react and generate the gas within the balloon.

11. The method of claim 10, wherein the swallowable device further comprises a communication hub disposed within the casing and coupled to the microcontroller, the communication hub configured to receive a remote signal and communicate the remote signal to the microcontroller.

12. The method of claim 10, further comprising:
receiving a remotely generated deflation signal; and
activating a deflation mechanism in response to the deflation signal to deflate the balloon by way of flow of the gas through the passage.

13. The method of claim 10, further comprising dissolving a dissolvable coating coated onto the balloon to release the balloon.

14. The method of claim 10, wherein the first substance is an acid in an aqueous solution and the second substance is a bicarbonate.

15. The method of claim 10, wherein the actuator comprises a stopper and a resilient member is held compressed by the stopper, and the stopper is configured to, when activated electrically, release the resilient member to drive the plunger.

* * * * *